(12) United States Patent
Kim et al.

(10) Patent No.: US 9,899,604 B2
(45) Date of Patent: Feb. 20, 2018

(54) COMPOUND FOR ORGANIC OPTOELECTRONIC DEVICE, ORGANIC LIGHT EMITTING DIODE INCLUDING THE SAME, AND DISPLAY INCLUDING THE ORGANIC LIGHT EMITTING DIODE

(71) Applicants: SAMSUNG ELECTRONICS CO., LTD., Suwon-si, Gyeonggi-do (KR); CHEIL INDUSTRIES INC., Gumi-si, Gyeongsangbuk-do (KR)

(72) Inventors: Sang Mo Kim, Hwaseong-si (KR); Jhun Mo Son, Yongin-si (KR); Ho Suk Kang, Suwon-si (KR); Yong Sik Jung, Seoul (KR); Hyeon Ho Choi, Seoul (KR); Kyu Young Hwang, Ansan-si (KR)

(73) Assignees: SAMSUNG ELECTRONICS CO., LTD., Gyeonggi-Do (KR); CHEIL INDUSTRIES INC., Gyeongsangbuk-Do (KR)

( * ) Notice: Subject to any disclaimer, the term of this patent is extended or adjusted under 35 U.S.C. 154(b) by 987 days.

(21) Appl. No.: 14/053,693

(22) Filed: Oct. 15, 2013

(65) Prior Publication Data

US 2014/0225083 A1 Aug. 14, 2014

(30) Foreign Application Priority Data

Feb. 13, 2013 (KR) ........................ 10-2013-0015398

(51) Int. Cl.
*H01L 51/00* (2006.01)
*C09K 11/06* (2006.01)
(Continued)

(52) U.S. Cl.
CPC ........ *H01L 51/0067* (2013.01); *C07D 401/14* (2013.01); *C07D 413/14* (2013.01);
(Continued)

(58) Field of Classification Search
CPC .... C07D 401/14; C07D 413/14; C09K 11/06; H01L 2251/308; H01L 51/0037;
(Continued)

(56) References Cited

U.S. PATENT DOCUMENTS 4,355,823 A * 10/1982 Burri ...................... B41M 5/136
106/31.19
5,968,674 A 10/1999 Hsieh et al.
(Continued)

FOREIGN PATENT DOCUMENTS

JP 2007197370 A 8/2007
JP 2010-272618 A * 12/2010
(Continued)

OTHER PUBLICATIONS

Machine translation for JP 2012-175025 A (publication date Sep. 2012).*
(Continued)

*Primary Examiner* — Dawn Garrett
(74) *Attorney, Agent, or Firm* — Cantor Colburn LLP

(57) ABSTRACT

A compound for an organic optoelectronic device represented by Chemical Formula 1

Chemical Formula 1

(Continued)

wherein groups $R_1$-$R_4$, $Ar_1$, $Ar_2$, $L_1$, $L_2$, X, $n_1$, and $n_2$ are described in the specification.

23 Claims, 3 Drawing Sheets

(51) Int. Cl.
  *C07D 401/14* (2006.01)
  *C07D 413/14* (2006.01)
  *H01L 51/50* (2006.01)

(52) U.S. Cl.
  CPC .......... *C09K 11/06* (2013.01); *H01L 51/0071* (2013.01); *H01L 51/0072* (2013.01); *H01L 51/0037* (2013.01); *H01L 51/0079* (2013.01); *H01L 51/5012* (2013.01); *H01L 2251/308* (2013.01); *Y02E 10/549* (2013.01)

(58) Field of Classification Search
  CPC ............ H01L 51/0067; H01L 51/0071; H01L 51/0072; H01L 51/0079; H01L 51/5012; Y02E 10/549
  See application file for complete search history.

(56) References Cited

U.S. PATENT DOCUMENTS

| | | | |
|---|---|---|---|
| 9,382,206 B2 | 7/2016 | Kato et al. | |
| 2002/0141032 A1 | 10/2002 | Guarr et al. | |
| 2009/0153031 A1* | 6/2009 | Kai | C07D 319/24 313/504 |
| 2010/0044695 A1* | 2/2010 | Kai | C07D 251/18 257/40 |
| 2012/0181524 A1 | 7/2012 | Kato et al. | |

FOREIGN PATENT DOCUMENTS

| | | | |
|---|---|---|---|
| JP | 2012-175025 A | * | 9/2012 |
| KR | 10-2010-0118700 A | | 11/2010 |
| KR | 10-2012-0104086 A | | 9/2012 |
| WO | 2010-126234 A1 | | 11/2010 |
| WO | 2012029253 A1 | | 3/2012 |

OTHER PUBLICATIONS

Machine translation for JP 2010-272618 A (publication date Dec. 2010).*

English Translation of the Office Action for Korean Application No. 10-2013-0015398.

Office Action dated Jul. 28, 2016 for the corresponding Korean Patent Application No. 10-2013-0015398.

Notice of Allowance dated Jan. 20, 2017, issued for the corresponding Korean Patent Application No. 10-2013-0015398, w/English Translation.

* cited by examiner

COMPOUND FOR ORGANIC OPTOELECTRONIC DEVICE, ORGANIC LIGHT EMITTING DIODE INCLUDING THE SAME, AND DISPLAY INCLUDING THE ORGANIC LIGHT EMITTING DIODE

CROSS-REFERENCE TO RELATED APPLICATION

This application claims priority to and the benefit of Korean Patent Application No. 10-2013-0015398 filed on Feb. 13, 2013, and all the benefits accruing therefrom under 35 U.S.C. §119, the content of which is incorporated herein in its entirety by reference.

BACKGROUND

1. Field

A compound for an organic optoelectronic device that provides an organic optoelectronic device having excellent life-span, efficiency, electrochemical stability, and thermal stability, an organic light emitting diode, and a display device including the organic light emitting diode are disclosed.

2. Description of the Related Art

An organic optoelectronic device is, in a broad sense, a device for transforming photo-energy to electrical energy, or conversely, a device for transforming electrical energy to photo-energy.

An organic optoelectronic device may be classified in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of the organic optoelectronic device include an organic light emitting diode, an organic solar cell, an organic photoconductor drum, an organic transistor, and the like, which require a hole injecting or transport material, an electron injecting or transport material, or a light emitting material.

Particularly, an organic light emitting diode ("OLED") has recently drawn attention due to an increasing demand for flat panel displays. In general, organic light emission refers to conversion of electrical energy into photo-energy.

Such an organic light emitting diode converts electrical energy into light by applying a current to an organic light emitting material. It has a structure in which a functional organic material layer is interposed between an anode and a cathode. The organic material layer includes a multi-layer including different materials, for example a hole injection layer ("HIL"), a hole transport layer ("HTL"), an emission layer, an electron transport layer ("ETL"), and an electron injection layer ("EIL"), in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic light emitting diode in addition to the fluorescent light emitting material. Such a phosphorescent material emits light by transporting the electrons from a ground state to an exited state, non-radiance transiting of a singlet exciton to a triplet exciton through intersystem crossing, and transiting the triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength, color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to achieve excellent performance in an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been entirely satisfactory so there is a need for a novel material. This material development is also required for other organic optoelectronic devices.

A low molecular organic light emitting diode is manufactured as a thin film in a vacuum deposition method, and can have good efficiency and life-span performance. A polymer organic light emitting diode manufactured in an Inkjet or spin coating method has an advantage of low initial cost and being large-sized.

Both low molecular organic light emitting and polymer organic light emitting diodes have an advantage of self-light emitting, high speed response, wide viewing angle, ultra-thinness, high image quality, durability, large driving temperature range, and the like. In particular, they have good visibility due to the self-light emitting characteristic compared with a conventional LCD (liquid crystal display) and have an advantage of decreasing thickness and weight of an LCD by up to a third, because they do not need a backlight.

In addition, since they have a response speed of a microsecond unit, which is 1,000 times faster than an LCD, they can realize a perfect motion picture without an after-image. Based on these advantages, they have been developed to have a remarkable 80 times the efficiency and more than 100 times the life-span since they first came out in the late 1980's. Recently, they have become rapidly larger such that a 40-inch organic light emitting diode panel is now possible.

They are simultaneously required to have improved luminous efficiency and life-span in order to be larger. Herein, their luminous efficiency requires smooth combination between holes and electrons in an emission layer. However, since an organic material in general has slower electron mobility than hole mobility, it has a drawback of inefficient combination between holes and electrons. Accordingly, increasing electron injection and mobility from a cathode and simultaneously preventing movement of holes is required.

In order to improve the life-span, it is desired to prevent material crystallization caused by Joule heat generated during device operation. Accordingly, there has been a strong need for an organic compound having excellent electron injection and mobility, and high electrochemical stability.

SUMMARY

A compound for an organic optoelectronic device that may act as a light emitting material or electron injection and/or transport material, and a light emitting host containing an appropriate dopant, is provided.

An organic light emitting diode having excellent life-span, efficiency, driving voltage, electrochemical stability, and thermal stability, and a display device including the same, are provided.

In an embodiment, a compound for an organic optoelectronic device represented by Chemical Formula 1 is provided.

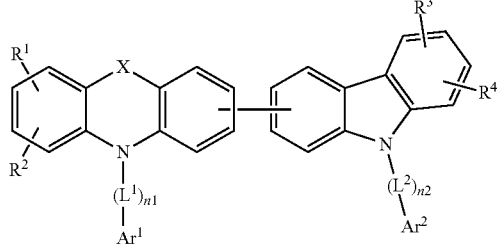

Chemical Formula 1

In Chemical Formula 1,

X is —NR'—, —S—, —SO$_2$—, —C(=O)—, or —O—, $R^1$ to $R^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, $L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, $Ar^1$ and $Ar^2$ are each independently a substituted or unsubstituted C6 to C30 aryl group or a substituted or unsubstituted C2 to C30 heteroaryl group, and at least one of $Ar^1$ and $Ar^2$ is a substituted or unsubstituted C2 to C30 heteroaryl group having electron characteristics.

The compound for an organic optoelectronic device may be represented by Chemical Formula 2.

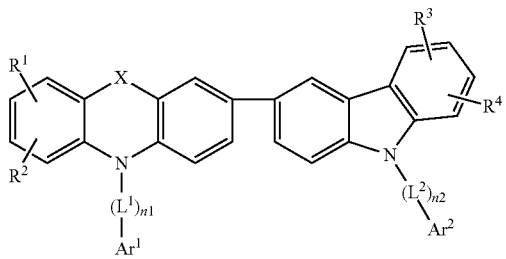

Chemical Formula 2

In Chemical Formula 2,

X is —NR'—, —S—, —SO$_2$—, —C(=O)—, or —O—, $R^1$ to $R^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, $L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, $Ar^1$ and $Ar^2$ are each independently a substituted or unsubstituted C6 to C30 aryl group or a substituted or unsubstituted C2 to C30 heteroaryl group, and at least one of $Ar^1$ and $Ar^2$ is a substituted or unsubstituted C2 to C30 heteroaryl group having electron characteristics.

The compound for an organic optoelectronic device may be represented by Chemical Formula 3.

Chemical Formula 3

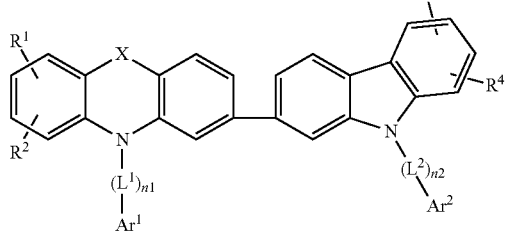

In Chemical Formula 3,

X is —NR'—, —S—, —$SO_2$—, —C(=O)—, or —O—, $R^1$ to $R^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, $L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, $Ar^1$ and $Ar^2$ are each independently a substituted or unsubstituted C6 to C30 aryl group or a substituted or unsubstituted C2 to C30 heteroaryl group, and at least one of $Ar^1$ and $Ar^2$ is a substituted or unsubstituted C2 to C30 heteroaryl group having electron characteristics.

The compound for an organic optoelectronic device may be represented by Chemical Formula 4.

Chemical Formula 4

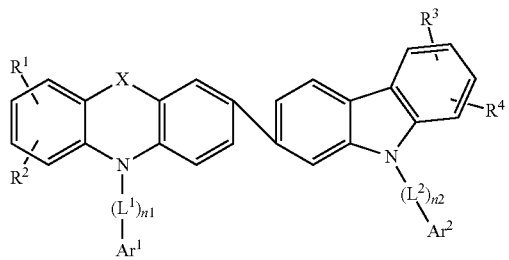

In Chemical Formula 4,

X is —NR'—, —S—, —$SO_2$—, —C(=O)—, or —O—, $R^1$ to $R^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, $L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, $Ar^1$ and $Ar^2$ are each independently a substituted or unsubstituted C6 to C30 aryl group or a substituted or unsubstituted C2 to C30 heteroaryl group, and at least one of $Ar^1$ and $Ar^2$ is a substituted or unsubstituted C2 to C30 heteroaryl group having electron characteristics.

The compound for an organic optoelectronic device may be represented by Chemical Formula 5.

Chemical Formula 5

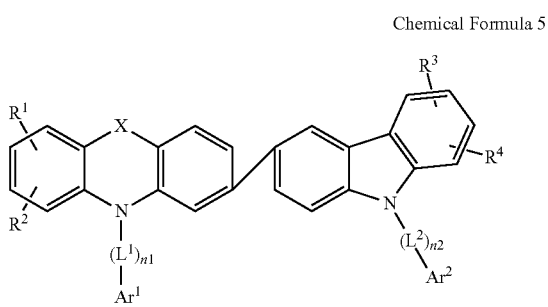

In Chemical Formula 5,

X is —NR'—, —S—, —SO$_2$—, —C(=O)—, or —O—,

R$^1$ to R$^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, L$^1$ and L$^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, Ar$^1$ and Ar$^2$ are each independently a substituted or unsubstituted C6 to C30 aryl group or a substituted or unsubstituted C2 to C30 heteroaryl group, and at least one of Ar$^1$ and Ar$^2$ is a substituted or unsubstituted C2 to C30 heteroaryl group having electron characteristics.

X may be —C(=O)— or —O—.

Ar$^1$ may be a substituted or unsubstituted C2 to C30 heteroaryl group having electron characteristics, and Ar$^2$ may be a substituted or unsubstituted C6 to C30 aryl group.

Ar$^2$ may be a substituted or unsubstituted C2 to C30 heteroaryl group having electron characteristics, and Ar$^1$ may be a substituted or unsubstituted C6 to C30 aryl group.

The substituted or unsubstituted C2 to C30 heteroaryl group having electron characteristics may be a substituted or unsubstituted quinolinylene group, a substituted or unsubstituted isoquinolinylene group, a substituted or unsubstituted pyridinylene group, a substituted or unsubstituted pyrimidinylene group, a substituted or unsubstituted triazinylene group, a substituted or unsubstituted furanyl group, a substituted or unsubstituted benzofuranyl group, a substituted or unsubstituted isofuranyl group, a substituted or unsubstituted benzoisofuranyl group, a substituted or unsubstituted oxazoline group, a substituted or unsubstituted benzoxazoline group, a substituted or unsubstituted oxadiazolyline group, a substituted or unsubstituted benzooxadiazolyline group, a substituted or unsubstituted thiophenyl group, a substituted or unsubstituted benzothiophenyl group, a substituted or unsubstituted isothiozoline group, a substituted or unsubstituted benzoisothiozoline group, a substituted or unsubstituted thiozoline group, a substituted or unsubstituted benzothiozoline group, a substituted or unsubstituted pyridazinyl group, a substituted or unsubstituted benzopyridazinyl group, a substituted or unsubstituted pyrazinyl group substituted or unsubstituted benzopyrazinyl group, or a combination thereof.

The substituted or unsubstituted C2 to C30 heteroaryl group having electron characteristics may be represented by one of Chemical Formulae X-1 to X-5.

Chemical Formula X-1

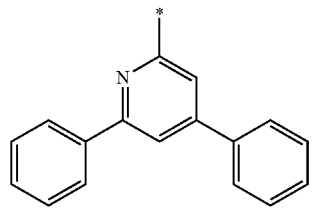

Chemical Formula X-2

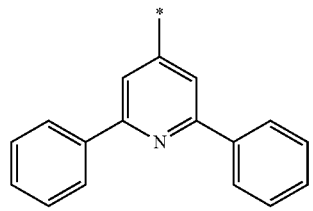

Chemical Formula X-3

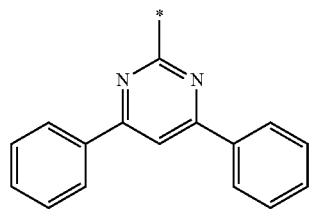

Chemical Formula X-4

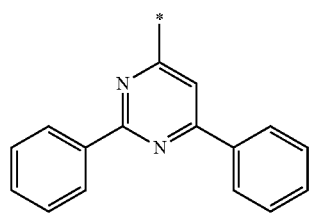

Chemical Formula X-5
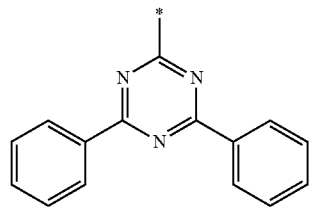
The compound for an organic optoelectronic device may be represented by one of Chemical Formulae A-1 to A-13.
A-1
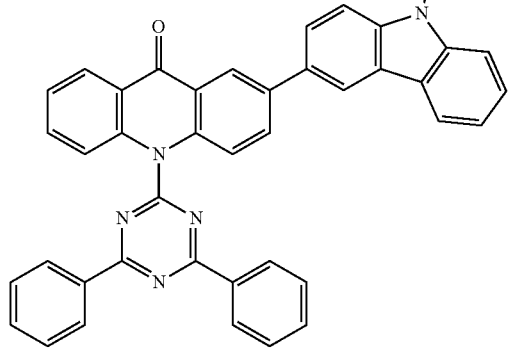
A-2
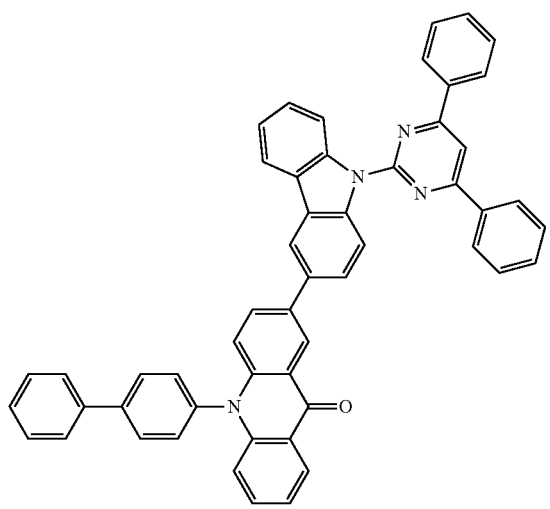
A-3
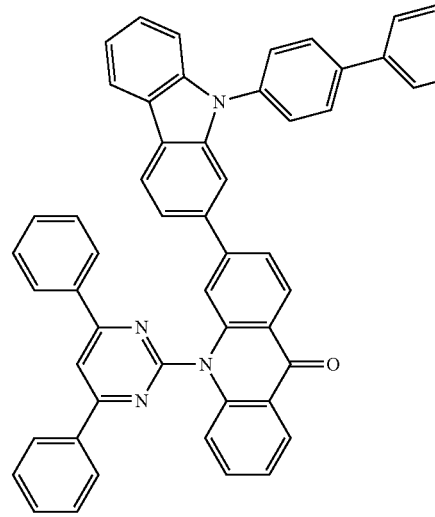
A-4
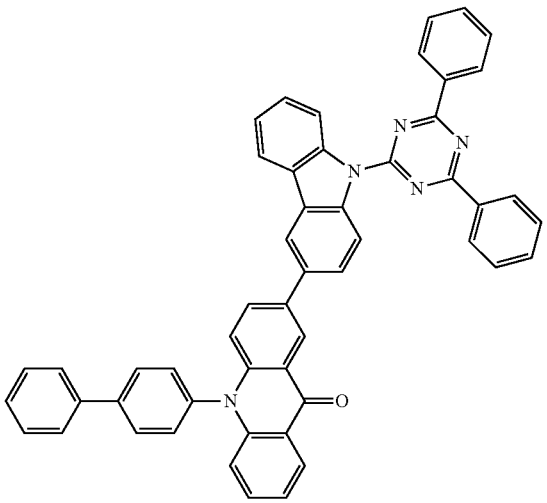
A-5
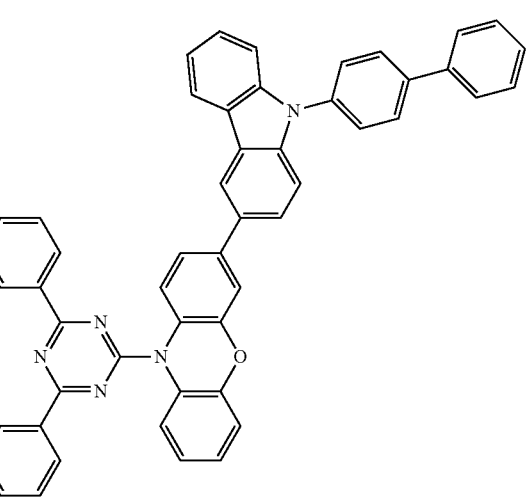

A-6
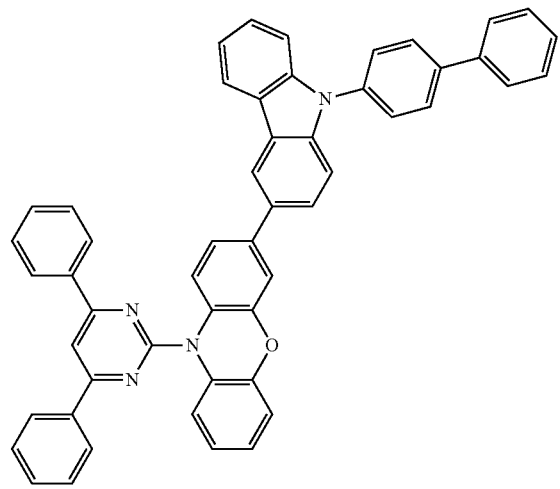
A-7
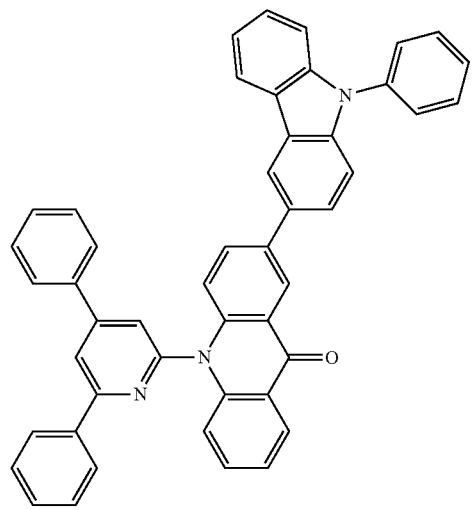
A-8
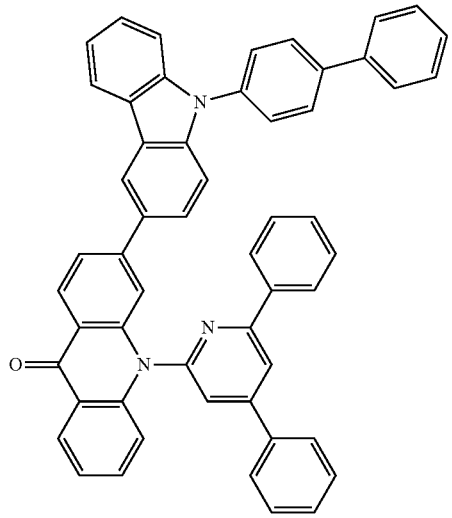
A-9
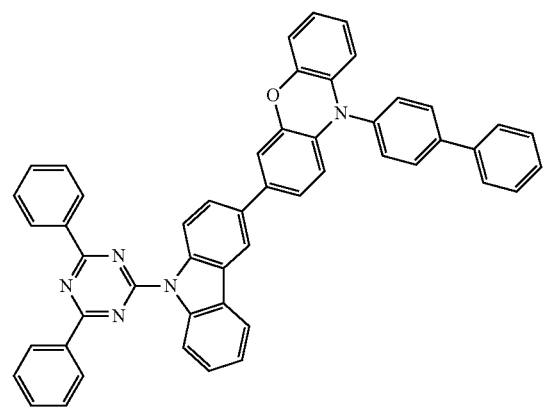
A-10
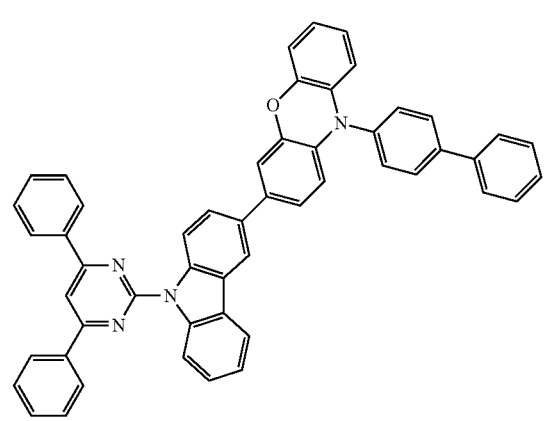
A-11
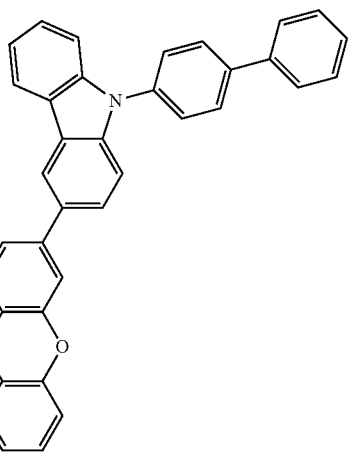

-continued

A-12

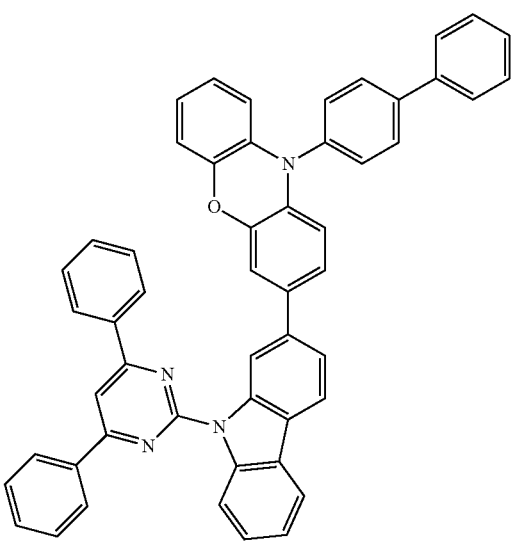

A-13

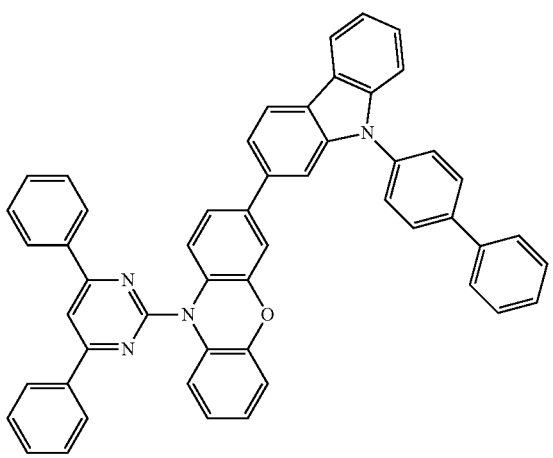

The organic optoelectronic device may be selected from an organic photoelectric device, an organic light emitting diode, an organic solar cell, an organic transistor, an organic photoconductor drum, and an organic memory device.

In another embodiment, an organic light emitting diode including an anode, a cathode, and at least one organic thin layer between the anode and the cathode is provided. The at least one organic thin layer includes the compound for an organic optoelectronic device described above.

The organic thin layer may be selected from an emission layer, a hole transport layer, a hole injection layer, an electron transport layer, an electron injection layer, a hole blocking layer, and a combination thereof.

The emission layer may include the compound for an organic optoelectronic device.

The emission layer may include a phosphorescent or fluorescent host material including the compound for an organic photoelectric device.

In yet another embodiment, a display device including the organic light emitting diode is provided.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
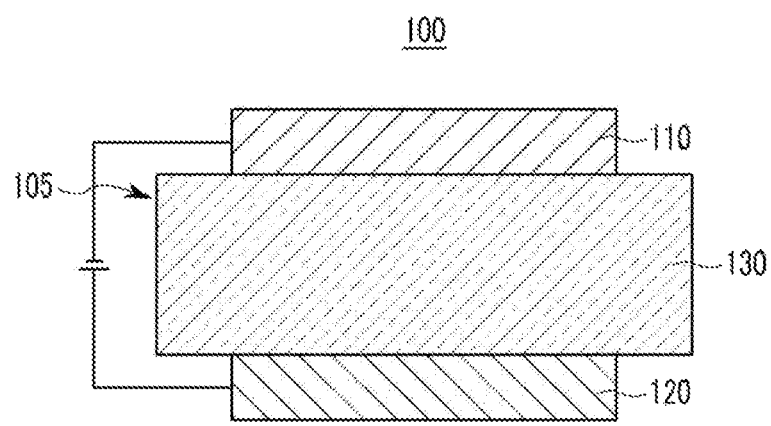
FIGS. 1 to 5 are cross-sectional views showing organic light emitting diodes according to various embodiments, including a compound for an organic optoelectronic device according to an embodiment.

Exemplary embodiments will hereinafter be described in detail. However, these embodiments are only exemplary, and the present disclosure is not limited thereto but rather is defined by the scope of the appended claims. Accordingly, the embodiments are merely described below, by referring to the figures, to explain aspects of the present description. As used herein, the term "and/or" includes any and all combinations of one or more of the associated listed items. The term "or" means "and/or." Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Additional aspects will be set forth in part in the description that follows and, in part, will be apparent from the description.

As used herein, when specific definition is not otherwise provided, the term "substituted" refers to a group substituted with deuterium, a halogen, a hydroxy group (—OH), an amino group (—NH$_2$), a carboxyl group (—CO$_2$H), a substituted or unsubstituted C1 to C30 amine group, a nitro group (—NO$_2$), a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group (—CF$_3$), and the like, or a cyano group (—CN) instead of at least one hydrogen of a substituted group or compound.

Two adjacent substituents selected from a halogen, a hydroxy group, an amino group, a substituted or unsubstituted C1 to C20 amine group, a nitro (—NO$_2$), a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group (—F), a trifluoroalkyl group such as a trifluoromethyl group (—CF$_3$), or a cyano group may be connected to each other to provide a ring.

As used herein, when specific definition is not otherwise provided, the term "hetero" refers to a group wherein one or more carbons are replaced with 1 to 3 hetero atoms selected from nitrogen (N), oxygen (O), sulfur (S), and phosphorus (P).

As used herein, when a definition is not otherwise provided, the term "combination thereof" refers to at least two substituents bound to each other by a linker, or at least two substituents fused to each other.

In the specification, when a definition is not otherwise provided, the term "alkyl group" may refer to an aliphatic hydrocarbon group. The alkyl group may be a saturated group without any double bond or triple bond.

The alkyl group may be branched, linear, or cyclic.

As used herein, the term "alkenyl group" may refer to a substituent including at least two carbon atoms and including at least one carbon-carbon double bond, and the "alkynyl group" may refer to a substituent including at least two carbon atoms and including at least one carbon-carbon triple bond.

The alkyl group may be a C1 to C20 alkyl group. For example, the alkyl group may be a C1 to C10 alkyl group or a C1 to C6 alkyl group.

For example, the C1 to C4 alkyl group may have 1 to 4 carbon atoms, and may be selected from methyl, ethyl, propyl, iso-propyl, n-butyl, iso-butyl, sec-butyl, and t-butyl.

Examples of the alkyl group may include a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, the term "alkoxy group" may refer to "alkyl-O—", wherein the alkyl is the same as described above and having the specified number of carbon atoms. Non-limiting examples of the alkoxy group include methoxy, ethoxy, propoxy, 2-propoxy, butoxy, t-butoxy, pentyloxy, hexyloxy, cyclopropoxy, and cyclohexyloxy.

The term "aromatic group" may refer to a cyclic substituent wherein all elements of the cycle having p-orbitals form one conjugation system. Examples of the aromatic group may include an aryl group and a heteroaryl group.

The "aryl group" may refer to a monocyclic or fused ring polycyclic (i.e., wherein the rings share adjacent pairs of carbon atoms) group.

As used herein, the term "aryloxy group" may refer to "—O-aryl" having the specified number of carbon atoms. A non-limiting example of the aryloxy group is phenoxy.

As used herein, the term "silyl group" may refer to a monovalent or higher valency group derived from a completely saturated, branched or unbranched (or a straight or linear) silane, and having the specified number of carbon atoms. A non-limiting example of silyl group is trimethylsilyl ((CH$_3$)$_3$Si—).

As used herein, the term "silyloxy group" may refer to "–O-silyl" having the specified number of carbon atoms. A non-limiting example of silyloxy group is trimethylsilyloxy ((CH$_3$)$_3$SiO—).

As used herein, the term "acyl group" may refer to "—C(=O)-alkyl" wherein the alkyl is the same as described above and having the specified number of carbon atoms. A non-limiting example of the acyl group is acetyl (CH$_3$C(=O)—).

As used herein, the term "alkoxycarbonyl group" may refer to "—C(=O)-alkyl" wherein the alkyl is the same as described above and having the specified number of carbon atoms. A non-limiting example of the alkoxycarbonyl group is methoxycarbonyl (CH$_3$C(=O)—).

As used herein, the term "acyloxy group" may refer to "–O-acyl" wherein the acyl is the same as described above and having the specified number of carbon atoms. A non-limiting example of the acyloxy group is acetyloxy (CH$_3$C(=O)O—).

As used herein, the term "acylamino group" may refer to "—NH-acyl" wherein the acyl is the same as described above and having the specified number of carbon atoms. A non-limiting example of the acylamino group is acetylamino (CH$_3$C(=O)NH—).

As used herein, the term "alkoxycarbonylamino group" may refer to "—NH—C(=O)—O-alkyl" wherein the alkyl is the same as described above and having the specified number of carbon atoms. A non-limiting example of the alkoxycarbonylamino group is methoxycarbonylamino (CH$_3$C(=O)NH—).

As used herein, the term "aryloxycarbonylamino group" may refer to "—NH—C(=O)—O-aryl" wherein the aryl is the same as described above and having the specified number of carbon atoms. A non-limiting example of the aryloxycarbonylamino group is phenoxycarbonylamino (PhOC(=O)NH—).

As used herein, the term "sulfamoylamino group" may refer to H$_2$NS(O$_2$)NH—, alkyl-NHS(O$_2$)NH—, (alkyl)$_2$NS(O$_2$)NH—, aryl-NHS(O$_2$)NH—, (aryl)$_2$NS(O)$_2$NH—, heteroaryl-NHS(O$_2$)—NH—, or (heteroaryl)$_2$NHS(O$_2$)—NH—, wherein alkyl, aryl, and heteroaryl are the same as described above and having the specified number of carbon atoms.

As used herein, the term "sulfonyl group" may refer to alkyl-S(O$_2$)—, aryl-S(O$_2$)—, or heteroaryl-S(O$_2$)—, wherein alkyl, aryl, and heteroaryl are the same as described above and having the specified number of carbon atoms.

As used herein, the term "alkylthio group" may refer to "alkyl-S—", wherein the alkyl is the same as described above and having the specified number of carbon atoms. Non-limiting example of the alkylthio group include methylthio.

As used herein, the term "arylthio group" may refer to "aryl-S—", wherein the aryl is the same as described above and having the specified number of carbon atoms. Non-limiting example of the arylthio group include phenylthio.

As used herein, the term "heterocyclothio group" may refer to "heterocyclo-S—", wherein the heterocyclo is a saturated hydrocarbon ring group, including at least one heteroatom selected from nitrogen (N), oxygen (O), phosphorous (P), and sulfur (S), wherein the rest of the cyclic atoms are carbon, and having the specified number of carbon atoms. A non-limiting example of a heterocycloalkyl group includes tetrahydro-2H-pyran-2-yl-thio-($OC_5H_9$—S—).

As used herein, the term "ureide group" may refer to $H_2NC(O)NH$—, alkyl-NHC(O)NH—, $(alkyl)_2NC(O)NH$—, aryl-NHC(O)NH—, $(aryl)_2NC(O)NH$—, heteroaryl-NHC(O)—NH—, or $(heteroaryl)_2NHC(O)NH$—, wherein alkyl, aryl, and heteroaryl are the same as described above and having the specified number of carbon atoms.

As used herein, the term "halogen" may refer to —F, —Cl, —Br, or —I.

As used herein, the term "ferrocenyl group" may refer to a monovalent or higher valency group derived from ferrocene (bis(η5-cyclopentadienyl)iron) by a removal of one or more hydrogen atoms.

As used herein, the term "alkenylene group" may refer to a straight or branched chain, divalent hydrocarbon group having at least one carbon-carbon double bond, and having the specified number of carbon atoms. A non-limiting example of the alkenylene group includes propenylene.

As used herein, the term "alkynylene group" may refer to a straight or branched chain, divalent hydrocarbon group having at least one carbon-carbon double bond, and having the specified number of carbon atoms. A non-limiting example of the alkynylene group includes propynylene.

As used herein, the term "arylene group" may refer to a divalent group formed by the removal of two hydrogen atoms from one or more rings of an arene, wherein the hydrogen atoms may be removed from the same or different rings. Non-limiting examples of the arylene group include phenylene or naphthylene.

As used herein, the term "heteroarylene group" may refer to a divalent group formed by the removal of two hydrogen atoms from one or more rings of a heteroaryl moiety, wherein the hydrogen atoms may be removed from the same or different rings, each of which rings may be aromatic or nonaromatic. A non-limiting example of the heteroarylene group includes pyrid-2,5-ylene.

As used herein, the term "heteroaryl group" may refer to an aryl group including 1 to 3 hetero atoms selected from nitrogen (N), oxygen (O), sulfur (S), and phosphorus (P), and remaining carbons in one functional group. The heteroaryl group may be a fused ring cyclic group where each cycle may include the 1 to 3 heteroatoms.

Non-limiting examples of a monocyclic heteroaryl group include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiaxolyl, 1,2,3-thiadiazolyl, 1,2,4-thiadiazolyl, 1,2,5-thiadiazolyl, 1,3,4-thiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, 2-pyrazin-2-yl, pyrazin-4-yl, pyrazin-5-yl, 2-pyrimidin-2-yl, 4-pyrimidin-2-yl, and 5-pyrimidin-2-yl.

Non-limiting examples of a bicyclic heteroaryl group include indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

In this specification, the term "hole characteristics" may refer to an ease with which a hole formed in the anode is injected into the emission layer and transported in the emission layer due to a conductive characteristic according to HOMO level. For example, the hole characteristics may be similar to electron-repelling characteristics.

In this specification, the term "electron characteristics" may refer to an ease with which an electron formed in the cathode is easily injected into the emission layer and transported in the emission layer due to a conductive characteristic according to LUMO level. For example, the hole characteristics are similar to electron-withdrawing characteristics.

A compound for an organic optoelectronic device according to an embodiment may include, for example, a multi-core structure wherein a phenoxazine or acridone; and carbazole are linked. The structure may selectively include various substituents.

The core structure may be used as a light emitting material, a hole injection material, or a hole transport material of an organic optoelectronic device. Particularly, it may be adapted for an electron injection material or an electron transport material.

The compound for an organic optoelectronic device may include a core part and various substituents for substituting the core part, and thus may have various energy band gaps.

The compound may have an appropriate energy level depending on the substituents, and thus may fortify electron transport capability and hole transport capability of an organic optoelectronic device and bring about excellent effects in terms of efficiency and driving voltage. It may also have excellent electrochemical and thermal stability and thus improve life-span characteristics during the operation of the organic optoelectronic device.

According to an embodiment, a compound for an organic optoelectronic device represented by the following Chemical Formula 1 is provided.

Chemical Formula 1

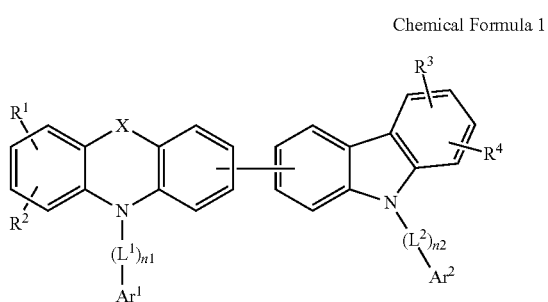

In Chemical Formula 1,

X is —NR'—, —S—, —SO$_2$—, —C(=O)— or —O—,

R$^1$ to R$^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, L$^1$ and L$^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, Ar$^1$ and Ar$^2$ are each independently a substituted or unsubstituted C6 to C30 aryl group or a substituted or unsubstituted C2 to C30 heteroaryl group, and at least one of Ar$^1$ and Ar$^2$ is a substituted or unsubstituted C2 to C30 heteroaryl group having electron characteristics.

In an embodiment, Ar$^1$ and Ar$^2$ are each independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triperylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but are not limited thereto.

A total conjugation length of the compound may be controlled by selecting L$^1$ and/or L$^2$ appropriately, and thereby a bandgap of triplet energy may be adjusted. Thereby, a material required for an organic optoelectronic device may be obtained. In addition, ortho, para, or meta binding positions may be used to adjust the triplet energy bandgap.

Examples of the L$^1$ and/or L$^2$ may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a substituted or unsubstituted p-terphenyl group, a substituted or unsubstituted m-terphenyl group, a substituted or unsubstituted pyrenylene group, and the like.

In an embodiment, the compound represented by the Chemical Formula 1 may be represented by the following Chemical Formula 2.

Chemical Formula 2

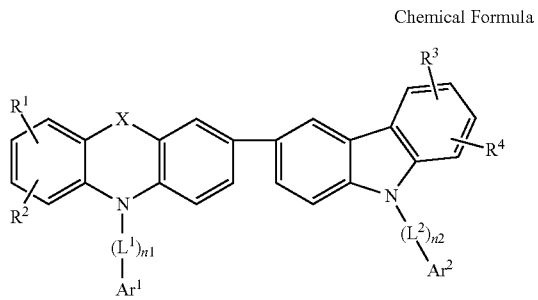

In Chemical Formula 2, definitions of groups R$_1$-R$_4$, Ar$_1$, Ar$_2$, L$_1$, L$_2$, X, n$_1$, and n$_2$ are the same as in Chemical Formula 1 and are not described herein. A multi-core structure as in Chemical Formula 2 may improve structural stability.

In an embodiment, the compound represented by the Chemical Formula 1 may be represented by the following Chemical Formula 3.

Chemical Formula 3

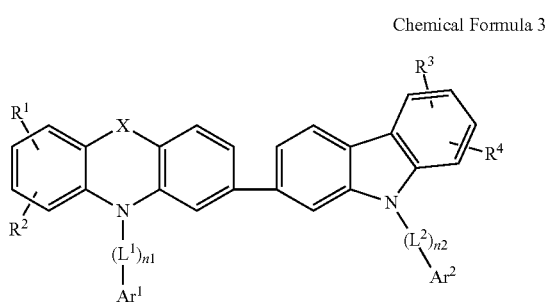

In Chemical Formula 3, definitions of groups $R_1$-$R_4$, $Ar_1$, $Ar_2$, $L_1$, $L_2$, X, $n_1$, and $n_2$ are the same as in Chemical Formula 1 and are not described herein. A multi-core structure as in Chemical Formula 3 may have high triplet energy due to decrease of a conjugation length.

In an embodiment, the compound represented by the Chemical Formula 1 may be represented by the following Chemical Formula 4.

Chemical Formula 4

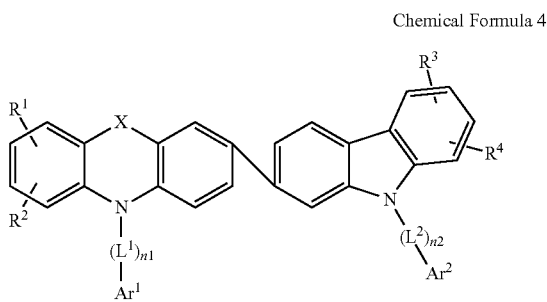

In Chemical Formula 4, definitions of groups $R_1$-$R_4$, $Ar_1$, $Ar_2$, $L_1$, $L_2$, X, $n_1$, and $n_2$ are the same as in Chemical Formula 1 and are not described herein. A multi-core structure as in Chemical Formula 4 may have high triplet energy due to decrease of a conjugation length.

In an embodiment, the compound represented by the Chemical Formula 1 may be represented by the following Chemical Formula 5.

Chemical Formula 5

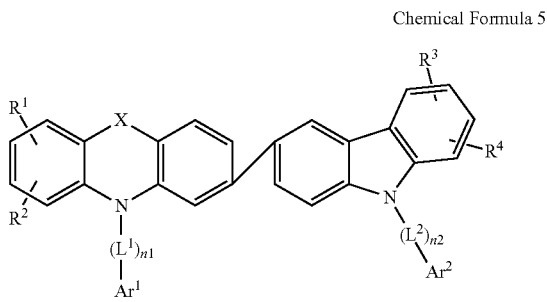

In Chemical Formula 5, definitions of groups $R_1$-$R_4$, $Ar_1$, $Ar_2$, $L_1$, $L_2$, X, $n_1$, and $n_2$ are the same as in Chemical Formula 1 and are not described. A multi-core structure as in Chemical Formula 5 may have high triplet energy due to decrease of a conjugation length.

In an embodiment, X may be —C(=O)— or —O—. When X is —C(=O)—, the compound may have high triplet energy. When X is —O—, structural electron mobility may be improved. However, the compound is not limited thereto.

$Ar^1$ may be a substituted or unsubstituted C2 to C30 heteroaryl group having electron characteristics, and $Ar^2$ may be a substituted or unsubstituted C6 to C30 aryl group. When $Ar^1$ is a substituted or unsubstituted C2 to C30 heteroaryl group having electron characteristics, a bandgap between HOMO energy and LUMO energy may increase.

$Ar^2$ may be a substituted or unsubstituted C2 to C30 heteroaryl group having electron characteristics, and $Ar^1$ may be a substituted or unsubstituted C6 to C30 aryl group. When $Ar^2$ is a substituted or unsubstituted C2 to C30 heteroaryl group having electron characteristics, structural hole mobility may be improved.

The substituted or unsubstituted C2 to C30 heteroaryl group having electron characteristics may be a substituted or unsubstituted quinolinylene group, a substituted or unsubstituted isoquinolinylene group, a substituted or unsubstituted pyridinylene group, a substituted or unsubstituted pyrimidinylene group, a substituted or unsubstituted triazinylene group, a substituted or unsubstituted furanyl group, a substituted or unsubstituted benzofuranyl group, a substituted or unsubstituted isofuranyl group, a substituted or unsubstituted benzoisofuranyl group, a substituted or unsubstituted oxazoline group, a substituted or unsubstituted benzoxazoline group, a substituted or unsubstituted oxadiazolyline group, a substituted or unsubstituted benzooxadiazolyline group, a substituted or unsubstituted thiophenyl group, a substituted or unsubstituted benzothiophenyl group, a substituted or unsubstituted isothiozoline group, a substituted or unsubstituted benzoisothiozoline group, a substituted or unsubstituted thiozoline group, a substituted or unsubstituted benzothiozoline group, a substituted or unsubstituted pyridazinyl group, a substituted or unsubstituted benzopyridazinyl group, a substituted or unsubstituted pyrazinyl group substituted or unsubstituted benzopyrazinyl group, or a combination thereof, but is not limited thereto.

In an embodiment, the substituted or unsubstituted C2 to C30 heteroaryl group having electron characteristics may be one of the following Chemical Formulae X-1 to X-5, but is not limited thereto.

Chemical Formula X-1

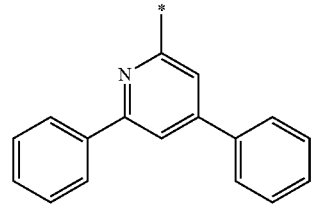

Chemical Formula X-2

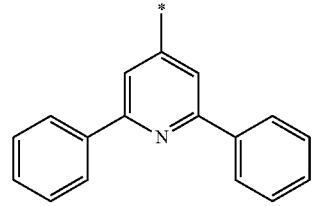

Chemical Formula X-3
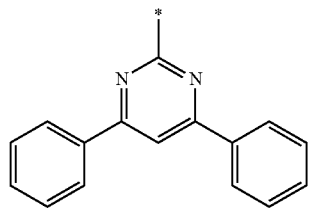
Chemical Formula X-4
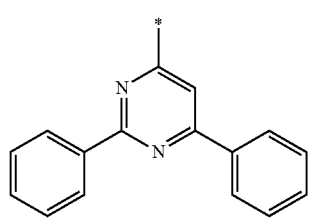
Chemical Formula X-5
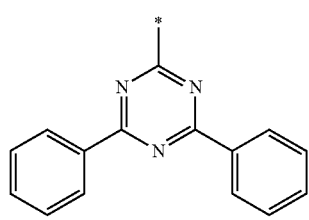
Specific examples of the compound for an organic optoelectronic device may be represented by one of the following compounds, but are not limited thereto.
A-1
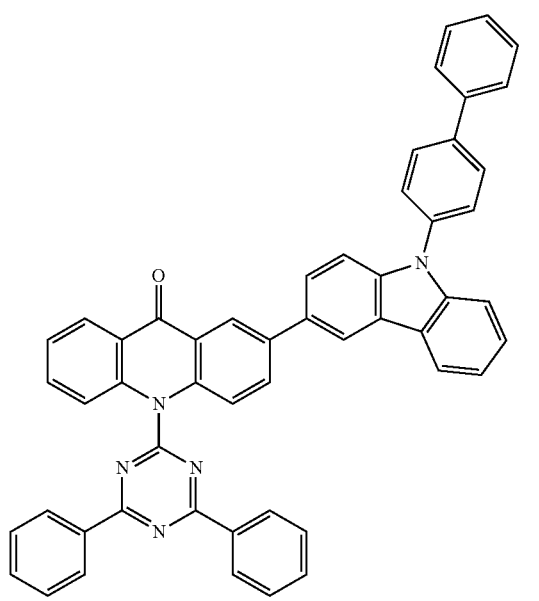
A-2
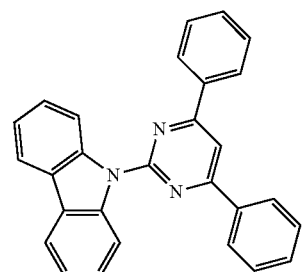
A-3
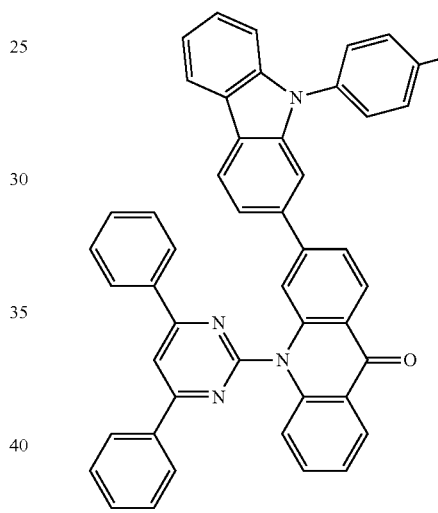
A-4
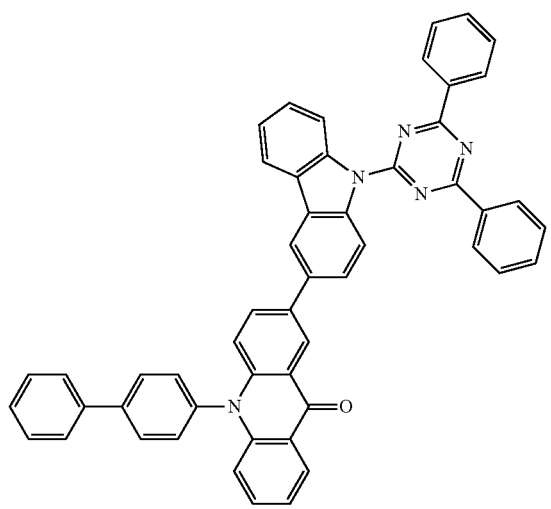

A-5
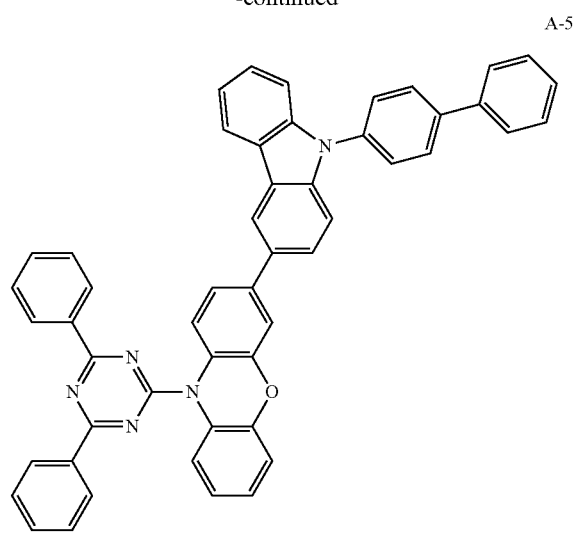
A-6
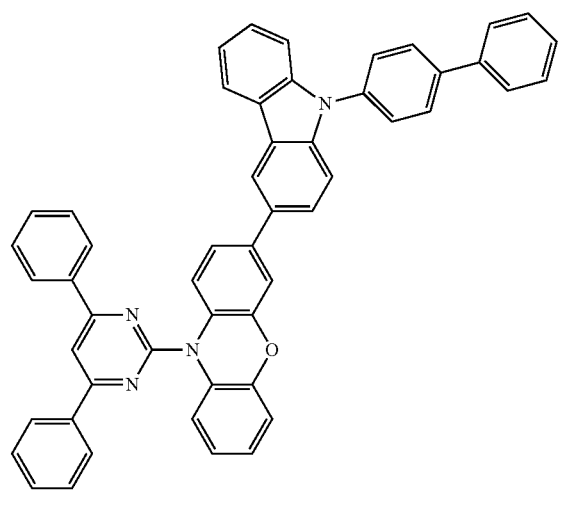
A-7
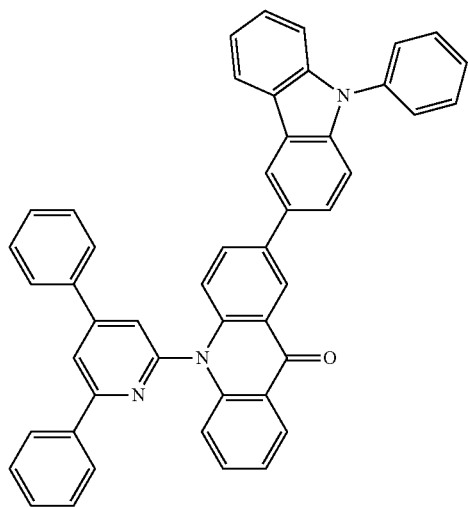
A-8
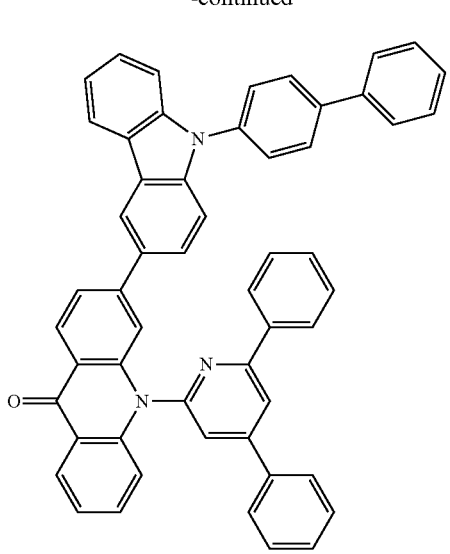
A-9
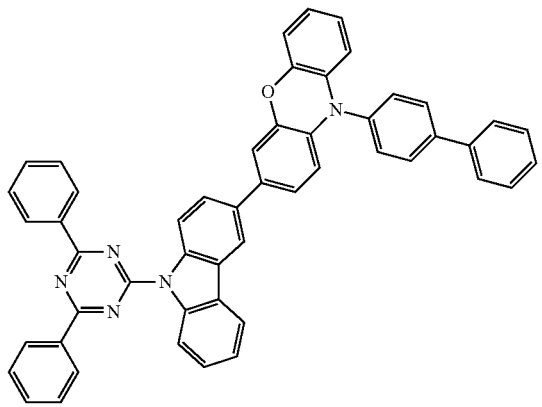
A-10
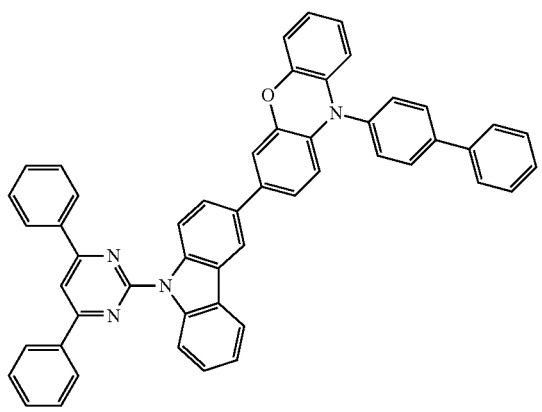

A-11

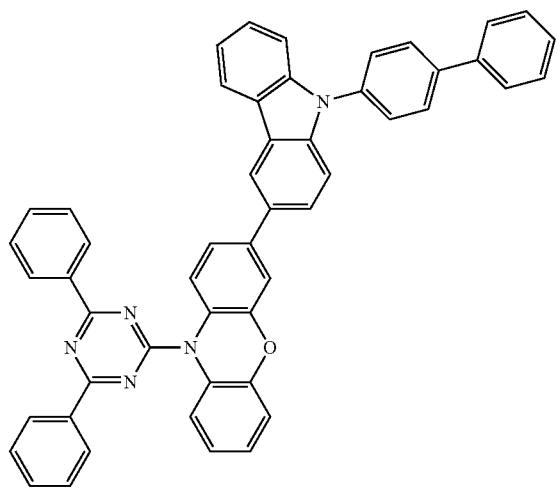

A-12

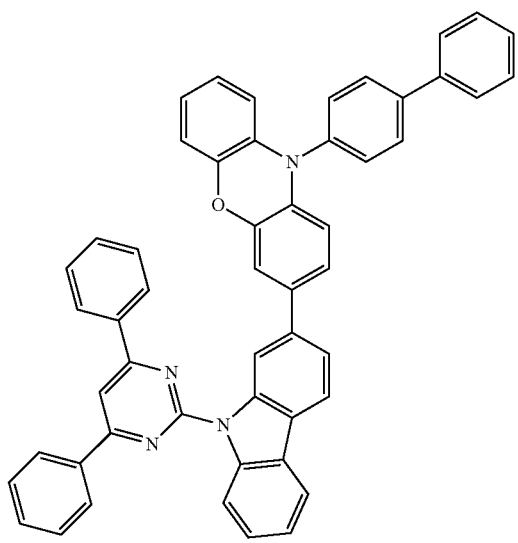

A-13

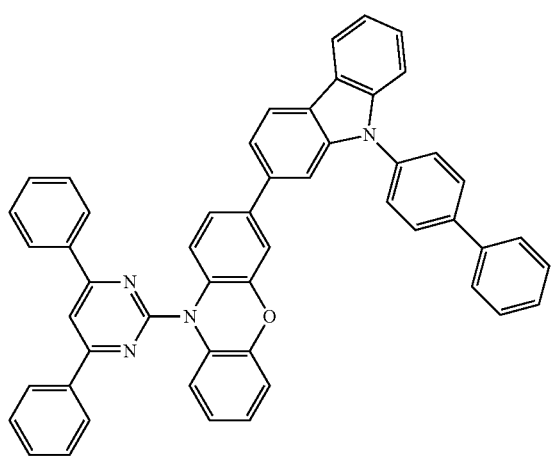

According to the embodiment, the compound includes a functional group having the electron characteristics when both electron and hole characteristics are desired, and thus may effectively improve the life-span of an organic light emitting diode and decrease a driving voltage thereof.

The compound for an organic optoelectronic device has a maximum light emitting wavelength in a range of about 320 to about 500 nanometers ("nm") and a triplet excited energy ("T1") ranging from greater than or equal to about 2.0 electron Volts ("eV"), and in an embodiment, from about 2.0 to about 4.0 eV, and thus may well transport a host charge having high triplet excited energy to a dopant and increase luminous efficiency of the dopant, and is also freely adjusted regarding HOMO and LUMO energy levels and decreases a driving voltage, and accordingly may be usefully applied as a host material or a charge transport material.

In addition, the compound for an organic optoelectronic device has photoactive and electrical activities, and thus may be usefully applied for a nonlinear optical material, an electrode material, a discolored material, a light switch, a sensor, a module, a wave guide, an organic transistor, a laser, a light absorbent, a dielectric material, a separating membrane, and the like.

The compound for an organic optoelectronic device including the above compounds has a glass transition temperature of greater than or equal to about 90° C. and a thermal decomposition temperature of greater than or equal to about 400° C., indicating improved thermal stability. Thereby, it is possible to produce an organic optoelectronic device having high efficiency.

The compound for an organic optoelectronic device including the above compounds may play a role of emitting light or injecting and/or transporting electrons, and may also act as a light emitting host with an appropriate dopant. In other words, the compound for an organic optoelectronic device may be used as a phosphorescent or fluorescent host material, a blue light emitting dopant material, or an electron transport material.

Since the compound for an organic optoelectronic device according to an embodiment is used for an organic thin layer, it may improve the life-span characteristics, efficiency characteristics, electrochemical stability, and thermal stability of an organic photoelectric device, and decrease the driving voltage.

Further, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photoconductor drum, an organic memory device, and the like. For example, the compound for an organic optoelectronic device according to an embodiment may be included in an electrode or an electrode buffer layer in an organic solar cell to improve the quantum efficiency, and it may be used as an electrode material for a gate, a source-drain electrode, or the like in the organic transistor.

Hereinafter, an organic light emitting diode is described.

According to another embodiment, an organic light emitting diode includes an anode, a cathode, and at least one organic thin layer between the anode and the cathode, and at least one organic thin layer may include the compound for an organic optoelectronic device according to an embodiment.

The organic thin layer that may include the compound for an organic optoelectronic device may include a layer selected from an emission layer, a hole transport layer ("HTL"), a hole injection layer ("HIL"), an electron transport layer ("ETL"), an electron injection layer ("EIL"), a hole blocking layer, and a combination thereof. The at least one layer includes the compound for an organic optoelectronic device according to an embodiment. Particularly, the compound for an organic optoelectronic device according to an embodiment may be included in a hole transport layer ("HTL") or a hole injection layer ("HIL"). In addition, when the compound for an organic optoelectronic device is included in the emission layer, the compound for an organic optoelectronic device may be included as a phosphorescent or fluorescent host.

FIGS. 1 to 5 are cross-sectional views showing organic light emitting diodes including the compound for an organic optoelectronic device according to an embodiment.

Referring to FIGS. 1 to 5, organic light emitting diodes 100, 200, 300, 400, and 500 according to an embodiment include at least one organic thin layer 105 interposed between an anode 120 and a cathode 110.

The anode 120 includes an anode material having capable of injecting holes into an organic thin layer. The anode material may include: a metal such as nickel, platinum, vanadium, chromium, copper, zinc, and gold, or alloys thereof; a metal oxide such as zinc oxide, indium oxide, indium tin oxide ("ITO"), and indium zinc oxide ("IZO"); a combination of a metal and oxide such as ZnO:Al and $SnO_2$:Sb; or a conductive polymer such as poly(3-methylthiophene), poly[3,4-(ethylene-1,2-dioxy)thiophene] ("PEDT"), polypyrrole, and polyaniline, but is not limited thereto. In an embodiment, it is preferable to include a transparent electrode including indium tin oxide ("ITO") as an anode.

The cathode 110 includes a cathode material having a small work function to help electron injection into an organic thin layer. The cathode material includes: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto. In an embodiment, it is preferable to include a metal electrode including aluminum as a cathode.

Referring to FIG. 1, the organic photoelectric device 100 includes an organic thin layer 105 including only an emission layer 130.

Figure 2:
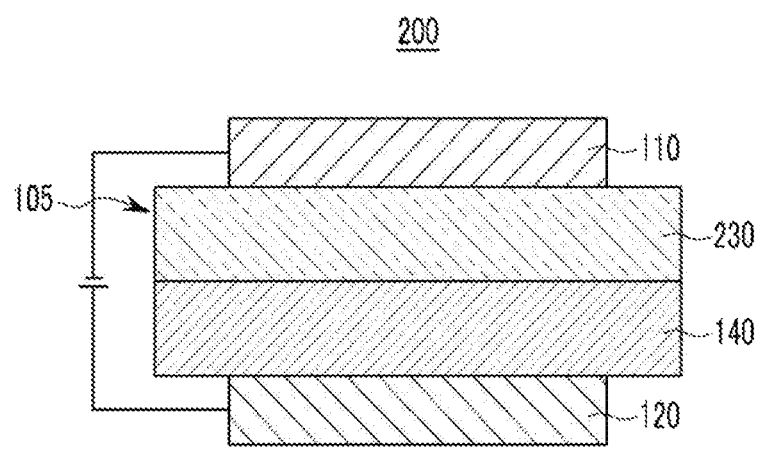

Referring to FIG. 2, a double-layered organic photoelectric device 200 includes an organic thin layer 105 including an emission layer 230 including an electron transport layer ("ETL"), and a hole transport layer ("HTL") 140. As shown in FIG. 2, the organic thin layer 105 includes a double layer of the emission layer 230 and the hole transport layer ("HTL") 140. The emission layer 130 (shown in FIG. 1) also functions as an electron transport layer ("ETL"), and the hole transport layer ("HTL") 140 layer has an excellent binding property with a transparent electrode such as ITO or an excellent hole transport capability.

Figure 3:
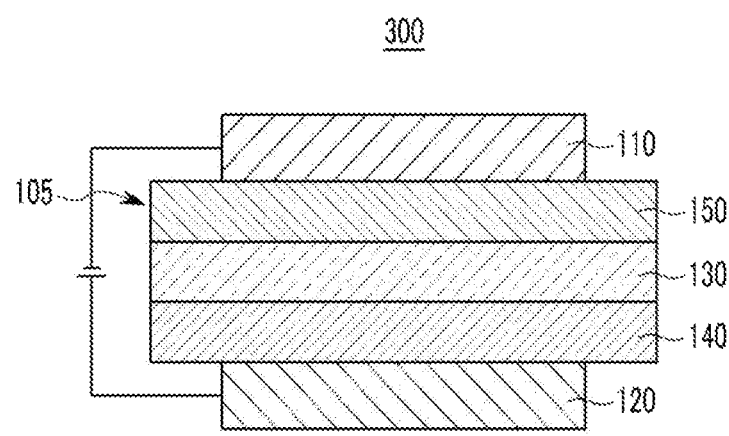

Referring to FIG. 3, a three-layered organic photoelectric device 300 includes an organic thin layer 105 including an electron transport layer ("ETL") 150, an emission layer 130, and a hole transport layer ("HTL") 140. The emission layer 130 is independently installed, and layers having an excellent electron transport capability or an excellent hole transport capability are separately stacked.

Figure 4:
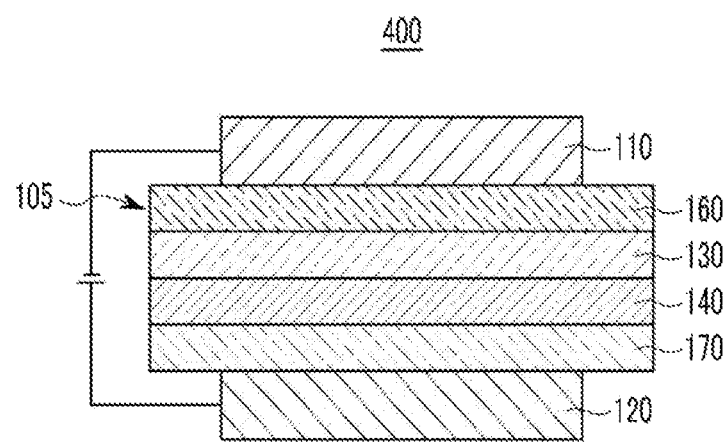

As shown in FIG. 4, a four-layered organic photoelectric device 400 includes an organic thin layer 105 including an electron injection layer ("EIL") 160, an emission layer 130, a hole transport layer ("HTL") 140, and a hole injection layer ("HIL") 170 for adherence with the cathode of ITO.

Figure 5:
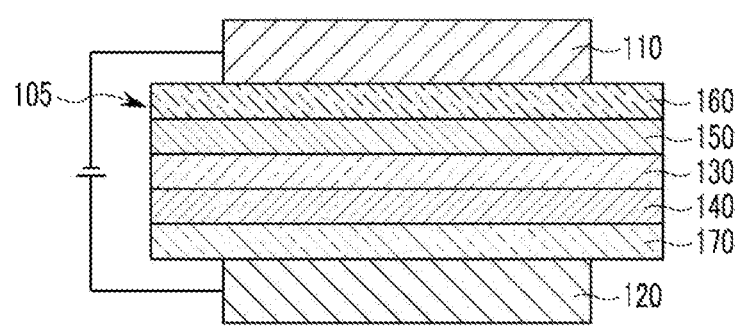

As shown in FIG. 5, a five-layered organic photoelectric device 500 includes an organic thin layer 105 including an electron transport layer ("ETL") 150, an emission layer 130, a hole transport layer ("HTL") 140, and a hole injection layer ("HIL") 170, and further includes an electron injection layer ("EIL") 160 to achieve a low voltage.

In FIGS. 1 to 5, the organic thin layer 105 including at least one selected from an electron transport layer ("ETL") 150, an electron injection layer ("EIL") 160, emission layers 130 and 230, a hole transport layer ("HTL") 140, a hole injection layer ("HIL") 170, and combinations thereof includes a compound for an organic optoelectronic device. The compound for an organic optoelectronic device may be used for an electron transport layer ("ETL") 150 including the electron transport layer ("ETL") 150 or electron injection layer ("EIL") 160. When it is used for the electron transport layer ("ETL"), it is possible to provide an organic photoelectric device having a more simple structure because it does not require an additional hole blocking layer (not shown).

Furthermore, when the compound for an organic photoelectric device is included in the emission layers 130 and 230, the material for the organic photoelectric device may be included as a phosphorescent or fluorescent host.

The organic light emitting diode may be fabricated by: forming an anode on a substrate; forming an organic thin layer in accordance with a dry coating method such as evaporation, sputtering, plasma plating, and ion plating, or a wet coating method such as spin coating, dipping, and flow coating; and providing a cathode thereon.

Another embodiment provides a display device including the organic photoelectric device according to the above embodiment.

Hereinafter, the embodiments are illustrated in more detail with reference to examples. These examples, however, should not in any sense be interpreted as limiting the scope of the present disclosure.

EXAMPLES

Preparation of Compound for Organic Optoelectronic Device

Example 1

Synthesis of Compound A-1

The compound A-1, an example of a compound for an organic optoelectronic device according to the present disclosure, is synthesized according to the following Reaction Scheme 1.

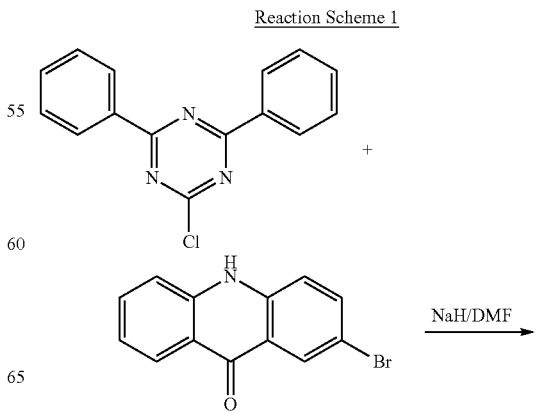

Reaction Scheme 1

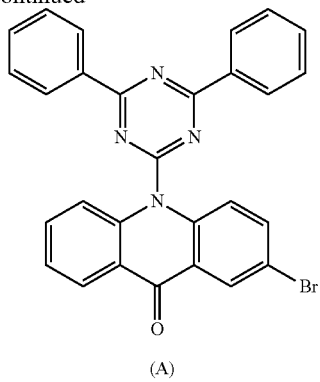

(A)

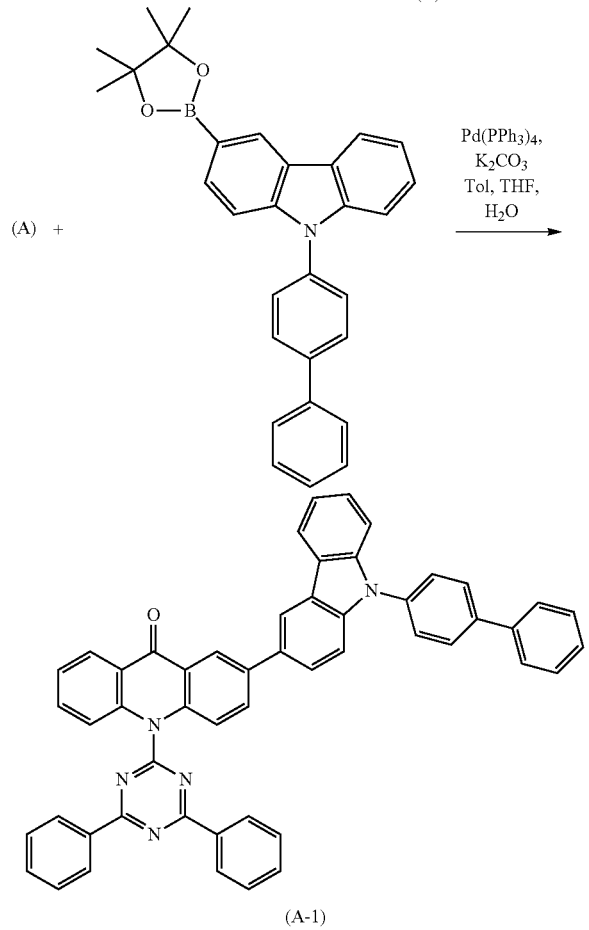

(A-1)

First Step: Synthesis of Intermediate Product (A)

3.30 g (11.87 mmol) of 2-bromoacridin-9(10H)-one is dissolved in 80 ml of DMF, and the reaction solution is cooled down to 0° C. Next, 0.5 g (13.06 mmol) of sodium hydride (NaH) is slowly added to the reaction solution, and the mixture is agitated at room temperature (20 to 30° C.) for one hour. Then, 3.8 g (14.25 mmol) of 2-chloro-4,6-diphenyl-1,3,5-triazine is added to the reactant. The resulting mixture is heated and agitated at 60° C. for 10 hours. When the reaction is complete, 200 ml of water is added to the agitated product, and the mixture is agitated at room temperature for 10 minutes. Then, 40 ml of methylene chloride is used to obtain an extract therefrom by extracting three times. Next, 10 g of magnesium is added to the sulfate extract, and the mixture is agitated for 5 minutes and then filtered under a reduced pressure and concentrated under a reduced pressure. The concentrated product is separated through silica gel column chromatography (methanol:methylene chloride=1:20 <volume/volume>), obtaining 3.64 g of an intermediate compound (A) (yield: 61%).

Second Step: Synthesis of Chemical Formula A-1

3.40 g (6.72 mmol) of the intermediate compound A, 3.59 g (8.07 mmol) of 9-([1,1'-biphenyl]-4-yl)-3-(4,4,5,5-tetramethyl-1,3,2-dioxaborolan-2-yl)-9H-carbazole, 0.78 g (0.67 mmol) of tetrakis triphenylphosphine palladium (0) (Pd (PPh$_3$)$_4$), and 2.79 g (20.16 mmol) of potassium carbonate are put into a mixed solution prepared by mixing 15 mL of toluene, 15 mL of tetrahydrofuran, and 15 mL of water. The obtained mixture is refluxed and agitated. When the reaction is complete, the agitated mixture is cooled down to room temperature, and an aqueous solution layer is removed through extraction. The extract is filtered through silica gel under a reduced pressure and concentrated under a reduced pressure. The obtained product is separated through silica gel column chromatography (ethyl acetate:n-hexane=1:5 <volume/volume>), obtaining 1.87 g of a desired compound A-1 (a yield: 37%).

$^1$H-NMR (300 MHz, CDCl$_3$): 8.46-8.27 (m, 8H); 8.15-8.07 (dd, 2H); 7.83-7.34 (m, 22H); 7.30-7.23 (m, 1H)).

Example 2

Synthesis of Compound A-2

The compound A-2, as an example of a compound for an organic optoelectronic device according to the present disclosure, is synthesized according to the following Reaction Scheme 2.

Reaction Scheme 2

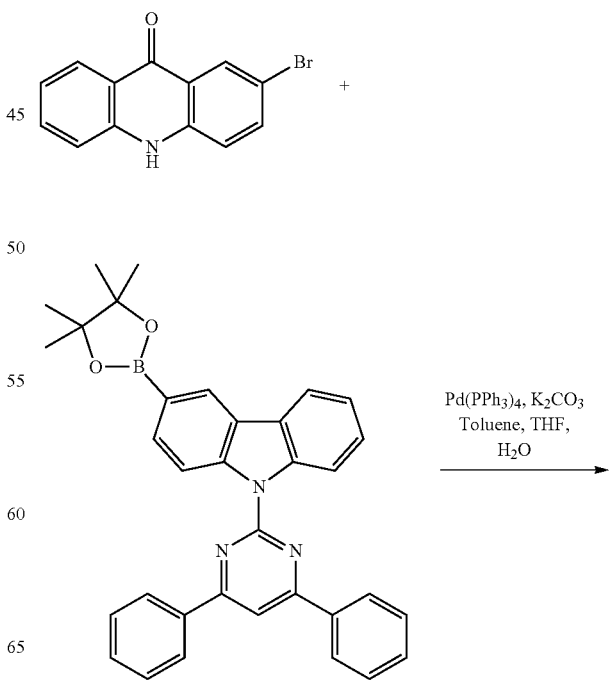

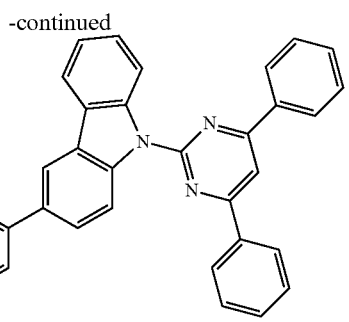

(B)

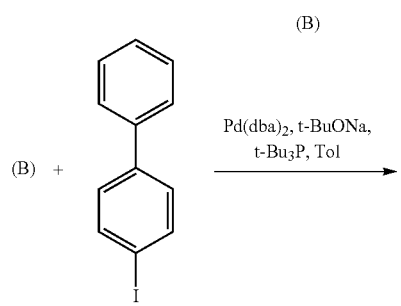

(B) + [4-iodobiphenyl]  →  Pd(dba)₂, t-BuONa, t-Bu₃P, Tol

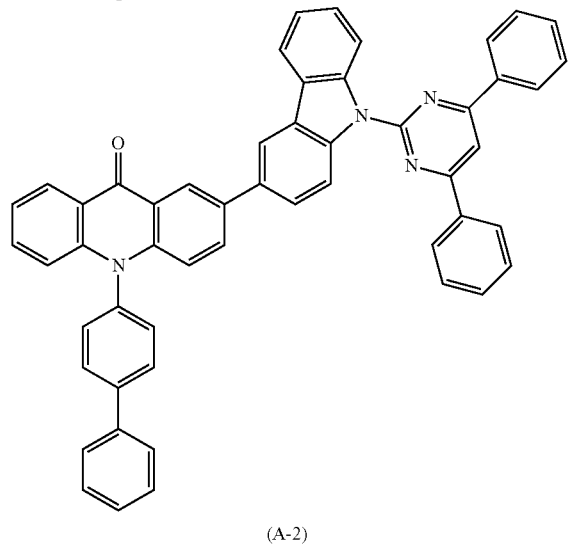

(A-2)

First Step: Synthesis of Intermediate Product (B)

5.00 g (18.28 mmol) of 2-bromoacridin-9(10H)-one, 11.46 g (21.94 mmol) of 9-(4,6-diphenylpyrimidin-2-yl)-3-(4,4,5,5-tetramethyl-1,3,2-dioxaborolan-2-yl)-9H-carbazole, 2.11 g (1.82 mmol) of tetrakis triphenylphosphine palladium (0) (Pd(PPh₃)₄), and 7.57 g (54.75 mmol) of potassium carbonate are put into a mixed solution prepared by mixing 30 mL of toluene, 30 mL of tetrahydrofuran, and 30 mL of water. The obtained mixture is refluxed and agitated. When the reaction is complete, the agitated mixture is cooled down to room temperature and precipitated in 1 L of methanol. The precipitate is extracted, and then heated and dissolved with 10 g of activated carbon in 3 L of 1,2-dichlorobenzene. The solution is filtered through silica gel under a reduced pressure. The filtered solution is concentrated down to 250 ml and then precipitated in 1 L of methanol, obtaining 6.23 g of an intermediate compound (B) (yield: 58%).

Second Step: Synthesis of Chemical Formula A-2

7.00 g (9.42 mmol) of the intermediate (B), 5.28 g (18.85 mmol) of 4-iodo-1,1'-biphenyl, 0.54 g (0.94 mmol) of Pd(dba)₂, 0.763 g (1.88 mmol) of tri-tert-butylphosphine ("TTBP"), and 1.81 g (18.85 mmol) of sodium tert-butoxide are put in 50 mL of toluene. The mixture is heated and agitated. When the reaction is complete, the agitated mixture is cooled down to room temperature and precipitated in methanol. The obtained precipitate is heated and dissolved in 2 L of 1,2-dichlorobenzene, and then filtered through silica gel under a reduced pressure. The filtered solution is concentrated down to 200 ml and then precipitated in 1 L of methanol, obtaining 2.71 g of a desired compound represented by Chemical Formula A-2 (a yield: 39%).

Example 3

Synthesis of Compound A-3

The compound A-3 as a specific example of a compound for an organic optoelectronic device according to the present disclosure, is synthesized according to the following Reaction Scheme 3.

Reaction Scheme 3

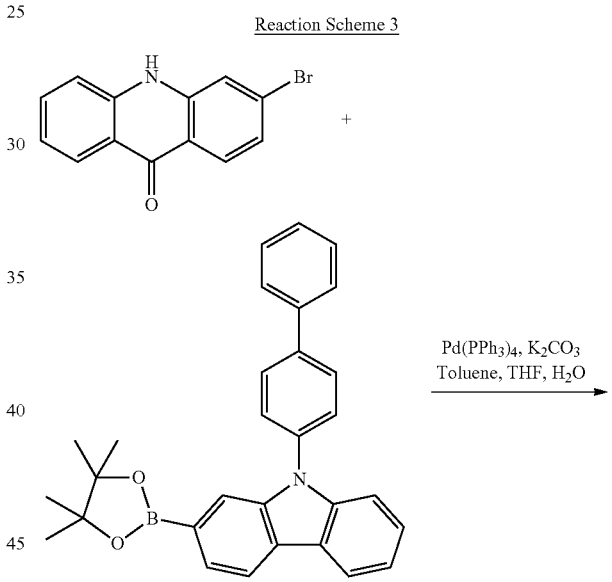

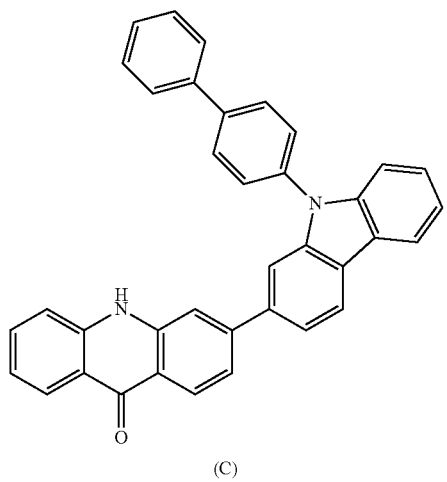

(C)

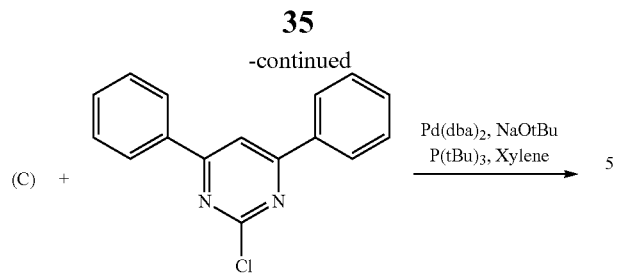

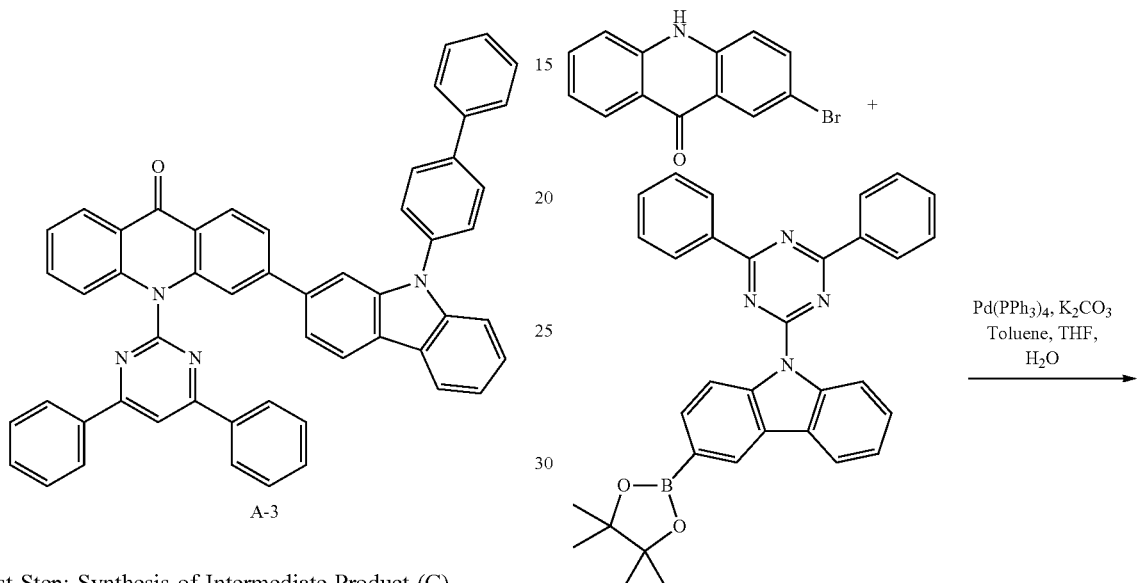

Example 4

Synthesis of Compound A-4

The compound A-4, as an example of a compound for an organic optoelectronic device according to the present disclosure, is synthesized according to the following Reaction Scheme 4.

Reaction Scheme 4

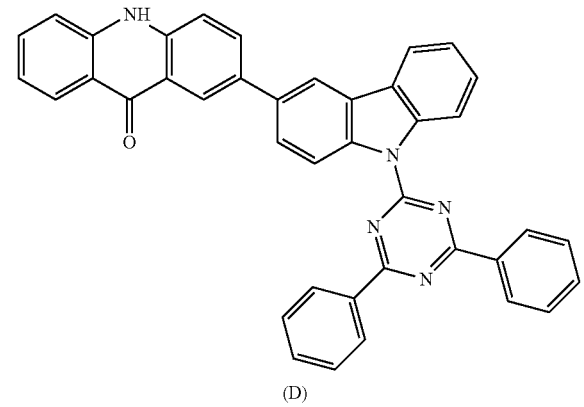

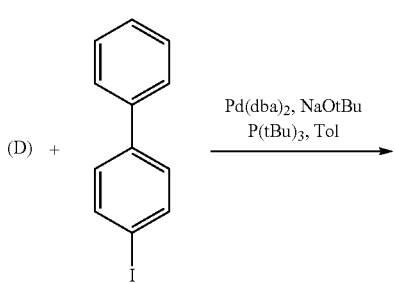

First Step: Synthesis of Intermediate Product (C)

5.00 g (18.24 mmol) of 3-bromoacridin-9(10H)-one (3-bromoacridin-9 10H-one), 9.75 g (21.89 mmol) of 9-([1,1'-biphenyl]-4-yl)-2-(4,4,5,5-tetramethyl-1,3,2-dioxaborolan-2-yl)-9H-carbazole, 2.11 g (1.82 mmol) of tetrakis triphenylphosphine palladium (0) (Pd(PPh$_3$)$_4$), and 7.56 g (54.72 mmol) of potassium carbonate are put in a mixed solution prepared by mixing 30 mL of toluene, 30 mL of tetrahydrofuran, and 30 mL of water, and the mixture is refluxed and agitated. When the reaction is complete, the agitated mixture is cooled down to room temperature and precipitated in 1 L of methanol, and then a precipitate produced therein is extracted and is heated and dissolved with 10 g of activated carbon in 3 L of 1,2-dichlorobenzene. The solution is filtered through silica gel under a reduced pressure. The filtered solution is concentrated down to 150 ml and precipitated in 1 L of methanol, obtaining 3.61 g of a compound, an intermediate C (yield: 39%).

Second Step: Synthesis of Chemical Formula A-3

3.60 g (9.42 mmol) of the intermediate compound (C), 3.76 g (14.08 mmol) of 2-chloro-4,6-diphenylpyrimidine, 0.41 g (0.70 mmol) of Pd(dba)$_2$, and 0.57 g (1.41 mmol) of tri-tert-butylphosphine ("TTBP"), and 1.35 g (14.08 mmol) of sodium tert-butoxide are put in 40 mL of xylene, and the mixture is heated and agitated. When the reaction is complete, the agitated mixture is cooled down to room temperature and precipitated in methanol. The precipitate is heated and dissolved in 2 L of 1,2-dichlorobenzene, and the solution is pressure-reducing filtered through silica gel. The filtered solution is concentrated down to 100 ml and precipitated in 1 L of methanol, obtaining 2.14 g of a compound represented by Chemical Formula A-3 (yield: 41%).

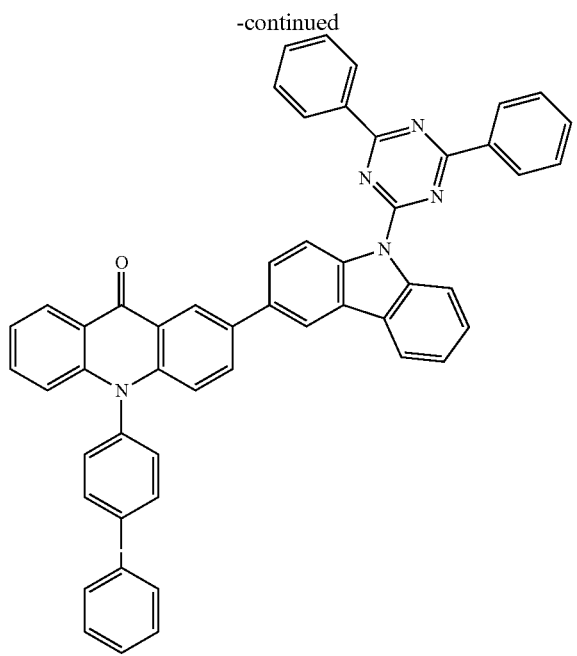

A-4

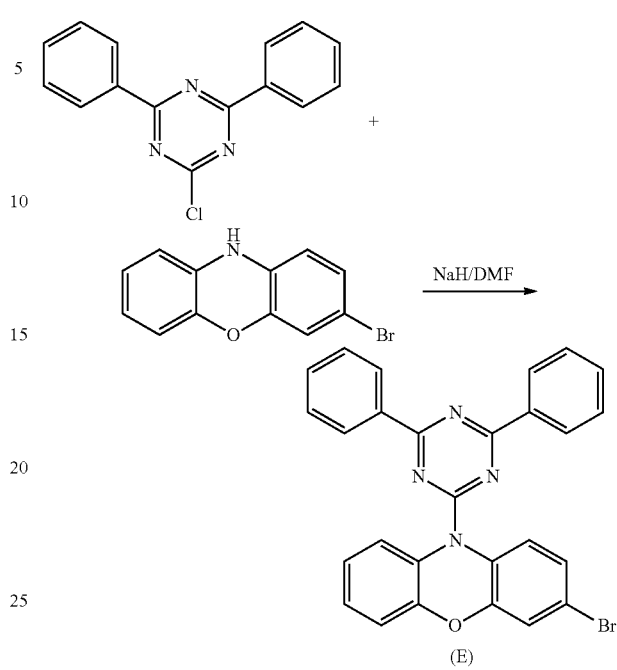

Reaction Scheme 5

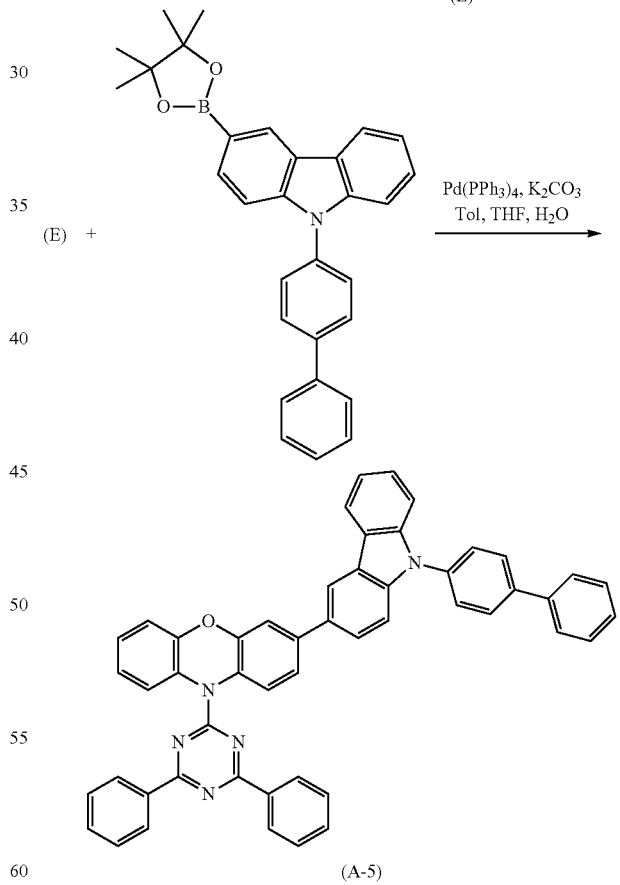

(A-5)

First Step: Synthesis of Intermediate Product (D)

5.00 g (18.25 mmol) of 2-bromoacridin-9(10H)-one, 11.49 g (21.90 mmol) of 9-(4,6-diphenyl-1,3,5-triazin-2-yl)-3-(4,4,5,5-tetramethyl-1,3,2-dioxaborolan-2-yl)-9H-carbazole, 2.11 g (1.83 mmol) of tetrakis triphenylphosphine palladium (0) (Pd(PPh$_3$)$_4$), and 7.57 g (54.76 mmol) of potassium carbonate are put into a mixed solution prepared by mixing 30 mL of toluene, 30 mL of tetrahydrofuran, and 30 mL of water, and the mixture is refluxed and agitated. When the reaction is complete, the agitated mixture is cooled down to room temperature and precipitated in 1 L of methanol, and a precipitate produced therein is extracted and is heated and dissolved with 10 g of activated carbon in 2 L of chlorobenzene. The solution is pressure-reducing filtered through silica gel. The filtered solution is concentrated into 200 ml and precipitated in 1 L of methanol, obtaining 4.69 g of an intermediate compound (D) (yield: 43%).

Second Step: Synthesis of Chemical Formula A-4

4.69 g (7.91 mmol) of the intermediate compound (D), 4.43 g (15.83 mmol) of 4-iodo-1,1'-biphenyl, 0.46 g (0.79 mmol) of Pd(dba)$_2$, 0.64 g (1.58 mmol) of tri-tert-butylphosphine ("TTBP"), and 1.52 g (15.83 mmol) of sodium tert-butoxide are put in 40 mL of toluene, and the mixture is heated and agitated. When the reaction is complete, the agitated mixture is cooled down to room temperature and precipitated in methanol, and the obtained precipitate is heated and dissolved in 2 L of chlorobenzene and then, pressure-reducing filtered through silica gel. The filtered solution is concentrated down to 100 ml and precipitated in 1 L of methanol, obtaining 3.24 g of a compound represented by Chemical Formula A-4 (yield: 55%).

Example 5

Synthesis of Compound A-5

The compound A-5, as an example of a compound for an organic optoelectronic device, is synthesized according to the following Reaction Scheme 5.

First Step: Synthesis of Intermediate Product (E)

5.00 g (19.09 mmol) of 3-bromo-10H-phenoxazine is dissolved in 80 ml of DMF, and the reaction solution is cooled down to 0° C. Next, 0.92 g (22.91 mmol) of sodium hydride (NaH) is slowly added to the reaction solution. The mixture is agitated at room temperature (20-30° C.) for one hour. Then, 6.13 g (22.91 mmol) of 2-chloro-4,6-diphenyl-1,3,5-triazine is added to the reactant, and the mixture is heated and agitated at room temperature for 10 hours. When the reaction is complete, 200 ml of water is added to the agitated mixture. The obtained mixture is agitated at room temperature for 10 minutes, and 40 ml of methylene chloride is used to perform an extraction three times. Then, 10 g of magnesium sulfate is added to the extract, and the mixture is agitated for 5 minutes and then filtered under a reduced pressure and concentrated under a reduced pressure. The concentrated product is recrystallized using ethyl acetate/n-hexane, obtaining 6.20 g of an intermediate compound (E) (yield: 66%).

Second Step: Synthesis of Chemical Formula A-5

6.20 g (12.56 mmol) of the intermediate compound (E), 6.72 g (15.09 mmol) of 9-([1,1'-biphenyl]-4-yl)-3-(4,4,5,5-tetramethyl-1,3,2-dioxaborolan-2-yl)-9H-carbazole, 1.45 g (1.26 mmol) of tetrakis triphenylphosphine palladium (0) (Pd(PPh$_3$)$_4$), and 5.21 g (37.72 mmol) of potassium carbonate are put in a mixed solution prepared by mixing 15 mL of toluene, 15 mL of tetrahydrofuran, and 15 mL of water, and the mixture is refluxed and agitated. When the reaction is complete, the agitated mixture is poured into 1 L of methanol to obtain a precipitate, and the precipitate is heated and dissolved in 500 ml of chlorobenzene. The solution is filtered through silica gel under a reduced pressure through acid clay/silica gel, obtaining 4.69 g of a compound A-5 (yield: 51%).

Example 6

Synthesis of Compound A-6

The compound A-6, as an example of a compound for an organic optoelectronic device according to the present disclosure, is synthesized according to the following Reaction Scheme 6.

Reaction Scheme 6

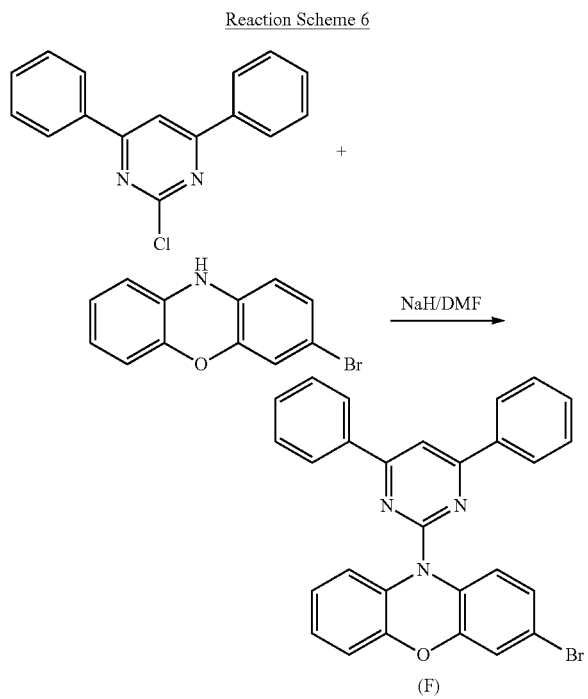

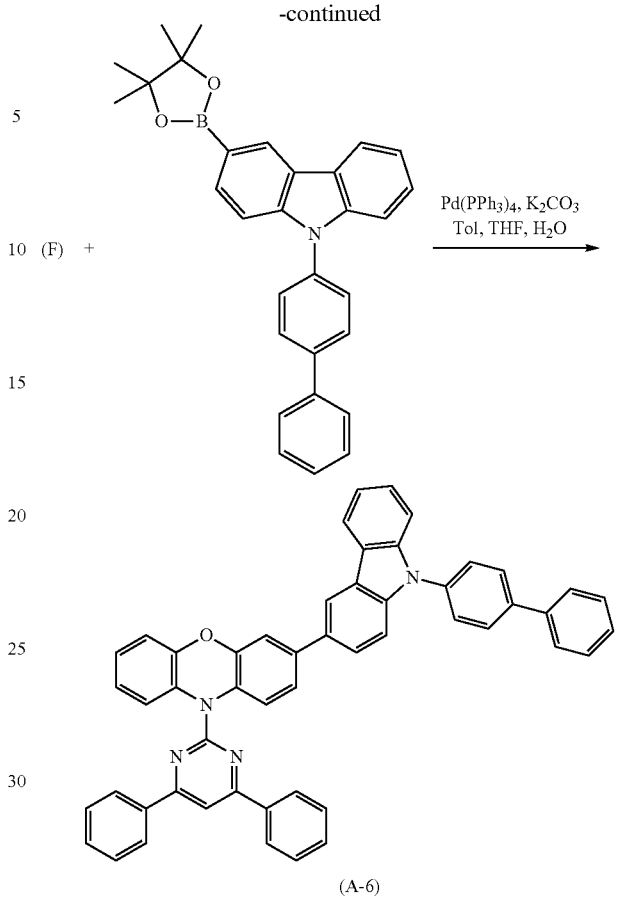

First Step: Synthesis of Intermediate Product (F)

5.00 g (19.09 mmol) of 3-bromo-10H-phenoxazine is dissolved in 80 ml of DMF, and the reaction solution is cooled down to 0° C. Next, 0.92 g (22.91 mmol) of sodium hydride (NaH) is slowly added to the reaction solution, and the mixture is agitated at room temperature (20-30° C.) for one hour. Then, 6.11 g (22.91 mmol) of 2-chloro-4,6-diphenylpyrimidine is added to the reactant, and the obtained mixture is agitated at room temperature. When the reaction is complete, 200 ml of water is added to the agitated mixture. The resulting mixture is agitated again at room temperature for 10 minutes, and 40 ml of methylene chloride is used to perform an extraction three times. Next, 10 g of magnesium sulfate is added to the extract, and the mixture is agitated for 5 minutes and then filtered under a reduced pressure and concentrated under a reduced pressure. The concentrated product is recrystallized using ethyl acetate/n-hexane, obtaining 5.81 g of an intermediate compound (E) (yield: 62%).

Second Step: Synthesis of Chemical Formula A-6

5.81 g (11.81 mmol) of the intermediate compound (F), 6.31 g (14.17 mmol) of 9-([1,1'-biphenyl]-4-yl)-3-(4,4,5,5-tetramethyl-1,3,2-dioxaborolan-2-yl)-9H-carbazole, 1.36 g (1.18 mmol) of tetrakis triphenylphosphine palladium (0) (Pd(PPh$_3$)$_4$), and 4.90 g (35.42 mmol) of potassium carbonate are put in a mixed solution prepared by mixing 20 mL of toluene, 20 mL of tetrahydrofuran, and 20 mL of water, and the mixture is refluxed and agitated. When the reaction is complete, the agitated mixture is poured into 1 L of methanol to obtain a precipitate. The precipitate is heated and dissolved in 1 L of chlorobenzene. The solution is filtered through acid clay/silica gel under a reduced pressure filter, and then heated again and filtered through silica gel under a reduced pressure, obtaining 5.10 g of a compound A-6 (yield: 59%).

Example 7

Synthesis of Compound A-7

The compound A-7, as an example of a compound for an organic optoelectronic device according to the present disclosure, is synthesized according to the following Reaction Scheme 7.

Reaction Scheme 7

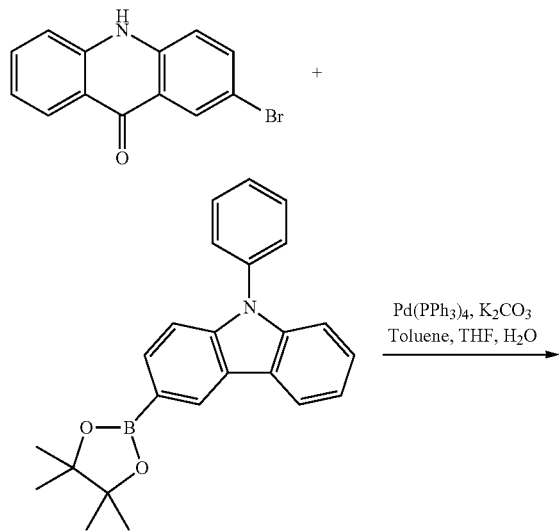

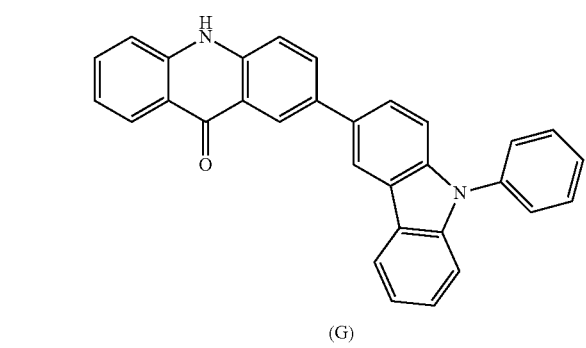

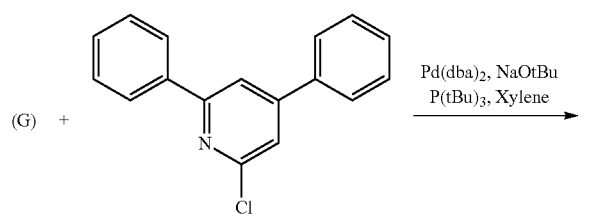

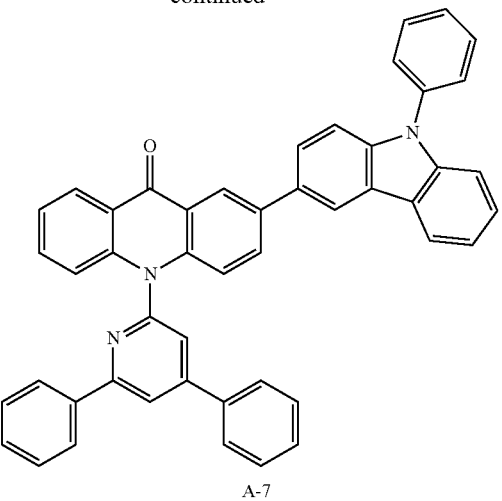

A-7

First Step: Synthesis of Intermediate Product (G)

5.00 g (18.24 mmol) of 2-bromoacridin-9(10H)-one, 8.08 g (21.88 mmol) of 9-phenyl-3-(4,4,5,5-tetramethyl-1,3,2-dioxaborolan-2-yl)-9H-carbazole, 2.11 g (1.82 mmol) of tetrakis triphenylphosphine palladium (0) (Pd(PPh$_3$)$_4$), and 7.56 g (54.71 mmol) of potassium carbonate are put into a mixed solution prepared by mixing 30 mL of toluene, 30 mL of tetrahydrofuran, and 30 mL of water, and the mixture is refluxed and agitated. When the reaction is complete, the agitated mixture is cooled down to room temperature and precipitated in 1 L of methanol. The precipitate is extracted, and then heated and dissolved in 2 L of 1,2-dichlorobenzene and pressure-reducing filtered through silica gel. The filtered solution is concentrated down to 200 ml and then precipitated in 1 L of methanol, obtaining 4.96 g of an intermediate compound (G) (yield: 62%).

Second Step: Synthesis of Chemical Formula A-7

4.96 g (11.35 mmol) of the intermediate compound (G), 6.03 g (22.71 mmol) of 2-chloro-4,6-diphenylpyridine, 0.65 g (1.14 mmol) of Pd(dba)$_2$, 0.92 g (2.27 mmol) of tri-tert-butylphosphine ("TTBP"), and 2.18 g (22.71 mmol) of sodium tert-butoxide are put in 60 mL of xylene, and the mixture is heated and agitated. When the reaction is complete, the agitated mixture is cooled down to room temperature and precipitated in methanol. The precipitate is heated and dissolved in 2 L of 1,2-dichlorobenzene and pressure-reducing filtered through silica gel. The filtered solution is concentrated down to 150 ml and precipitated in 1 L of methanol, obtaining 3.51 g of a compound represented by Chemical Formula A-7 (yield: 46%).

Example 8

Synthesis of A-8

The compound A-8, as an example of example of a compound for an organic optoelectronic device according to the present disclosure, is synthesized according to the following Reaction Scheme 8.

Reaction Scheme 8

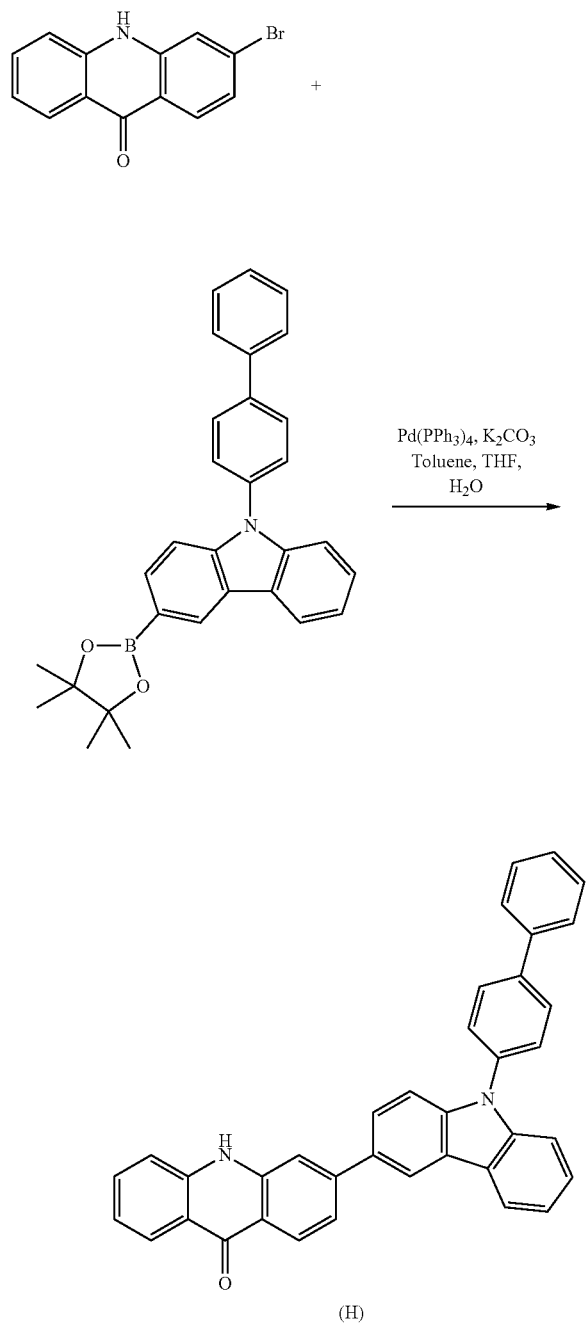

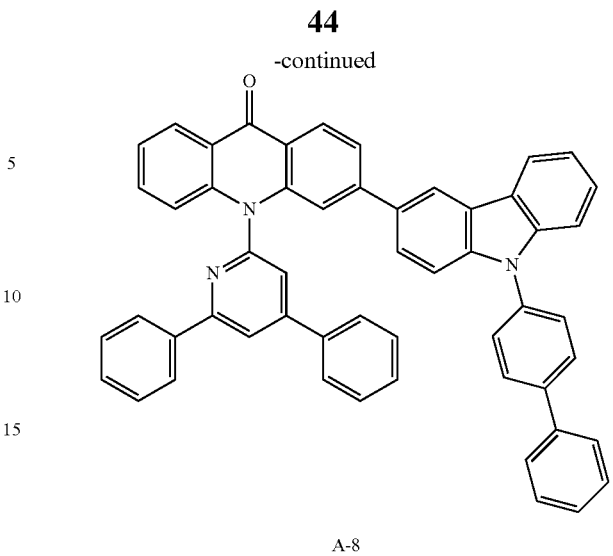

A-8

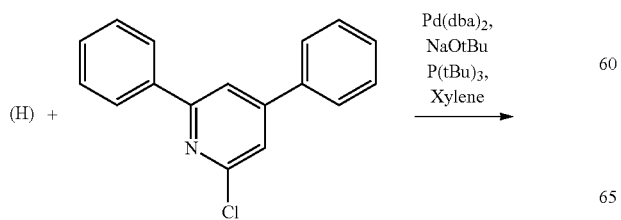

First Step: Synthesis of Intermediate Product (H)

5.00 g (18.24 mmol) of 3-bromoacridin-9(10H)-one, 9.75 g (21.89 mmol) of 9-([1,1'-biphenyl]-4-yl)-3-(4,4,5,5-tetramethyl-1,3,2-dioxaborolan-2-yl)-9H-carbazole, 2.11 g (1.82 mmol) of tetrakis triphenylphosphine palladium (0) (Pd(PPh$_3$)$_4$), and 7.56 g (54.73 mmol) of potassium carbonate are put in a mixed solution prepared by mixing 30 mL of toluene, 30 mL of tetrahydrofuran, and 30 mL of water, and the mixture is refluxed and agitated. When the reaction is complete, the agitated mixture is cooled down to room temperature and precipitated in methanol. Then, a precipitate produced therein is extracted, and then heated and dissolved in 3 L of 1,2-dichlorobenzene and pressure-reducing filtered through silica gel. The filtered solution is concentrated down to 200 ml and precipitated in 1 L of methanol, obtaining 6.27 g of an intermediate compound (H) (yield: 67%).

Second Step: Synthesis of Chemical Formula A-8

6.27 g (12.21 mmol) of the intermediate compound (H), 6.49 g (24.42 mmol) of 2-chloro-4,6-diphenylpyridine, 0.70 g (1.22 mmol) of Pd(dba)$_2$, 0.99 g (2.44 mmol) of tri-tert-butylphosphine ("TTBP"), and 2.35 g (24.42 mmol) of sodium tert-butoxide are put into 65 mL of xylene, and the mixture is heated and agitated. When the reaction is complete, the agitated mixture is cooled down to room temperature and precipitated in methanol. The obtained precipitate is heated and dissolved in 3 L of 1,2-dichlorobenzene and pressure-reducing filtered through silica gel. The filtered solution is concentrated down to 150 ml and precipitated in 1 L of methanol, obtaining 4.82 g of a compound represented by Chemical Formula A-8 (yield: 53%).

Example 9

Synthesis of Compound A-9

The compound A-9, as an example of a compound for an organic optoelectronic device according to the present disclosure, is synthesized according to the following Reaction Scheme 9.

Reaction Scheme 9

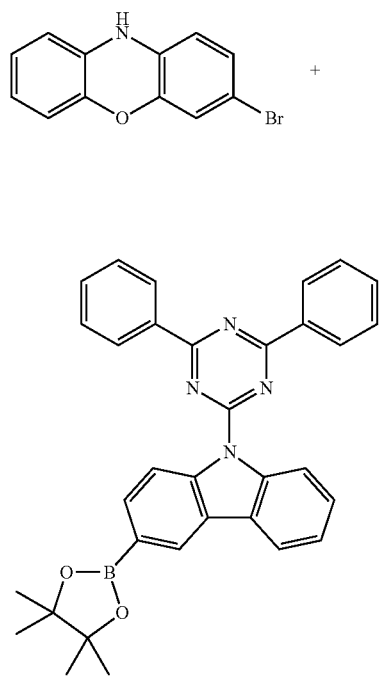

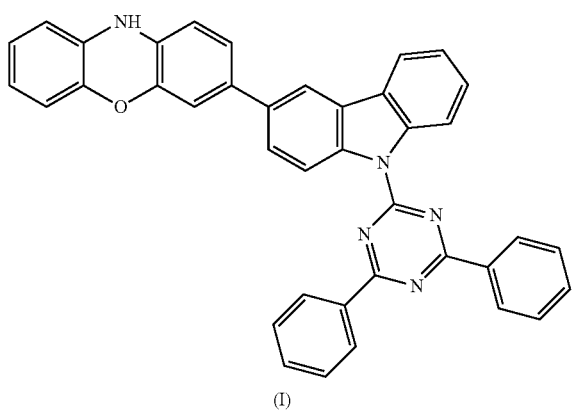

(I)

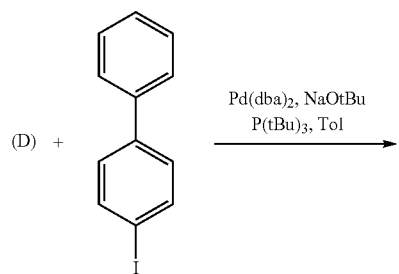

(D) +

Pd(dba)₂, NaOtBu
P(tBu)₃, Tol
→

-continued

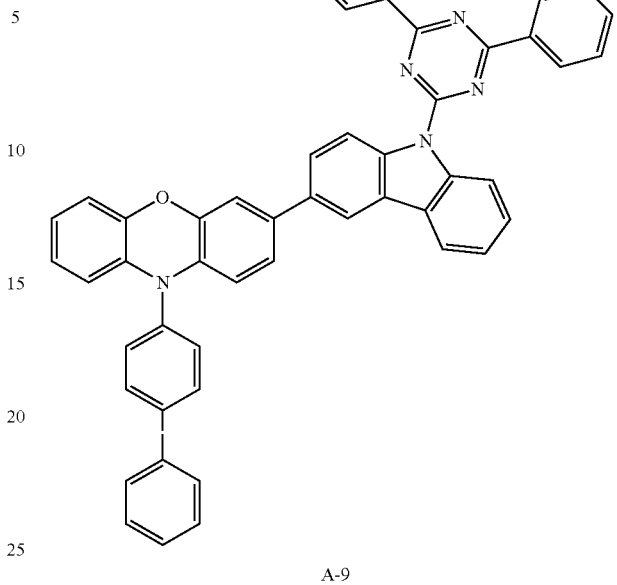

A-9

First Step: Synthesis of Intermediate Product (I)

5.00 g (19.08 mmol) of 3-bromo-10H-phenoxazine, 12.00 g (22.90 mmol) of 9-(4,6-diphenyl-1,3,5-triazin-2-yl)-3-(4,4,5,5-tetramethyl-1,3,2-dioxaborolan-2-yl)-9H-carbazole, 2.21 g (1.91 mmol) of tetrakis triphenylphosphine palladium (0) (Pd(PPh₃)₄), and 7.91 g (57.25 mmol) of potassium carbonate are put in a mixed solution prepared by mixing 30 mL of toluene, 30 mL of tetrahydrofuran, and 30 mL of water, and the mixture is refluxed and agitated. When the reaction is complete, the agitated mixture is cooled down to room temperature and precipitated in 1 L of methanol. The obtained precipitate is extracted, and then heated and dissolved in 2 L of chlorobenzene and pressure-reducing filtered through silica gel. The filtered solution is concentrated down to 200 ml and precipitated in 1 L of methanol, obtaining 5.72 g of an intermediate compound (I) (yield: 52%).

Second Step: Synthesis of Chemical Formula A-9

5.72 g (9.87 mmol) of the intermediate compound (I), 5.53 g (19.73 mmol) of 4-iodo-1,1'-biphenyl, 0.57 g (0.99 mmol) of Pd(dba)₂, 0.80 g (1.97 mmol) of tri-tert-butyl-phosphine ("TTBP"), and 1.90 g (19.73 mmol) of sodium tert-butoxide are put in 50 mL of toluene. The mixture is heated and agitated. When the reaction is complete, the agitated mixture is cooled down to room temperature and precipitated in methanol. The obtained precipitate is heated and dissolved in 1 L of chlorobenzene and pressure-reducing filtered through silica gel. The filtered solution is concentrated down to 100 ml and precipitated in 1 L of methanol, obtaining 4.56 g of a compound represented by Chemical Formula A-9 (yield: 63%).

Example 10

Synthesis of Compound A-10

The compound A-10, as an example of a compound for an organic optoelectronic device according to the present disclosure, is synthesized according to the following Reaction Scheme 10.

Reaction Scheme 10

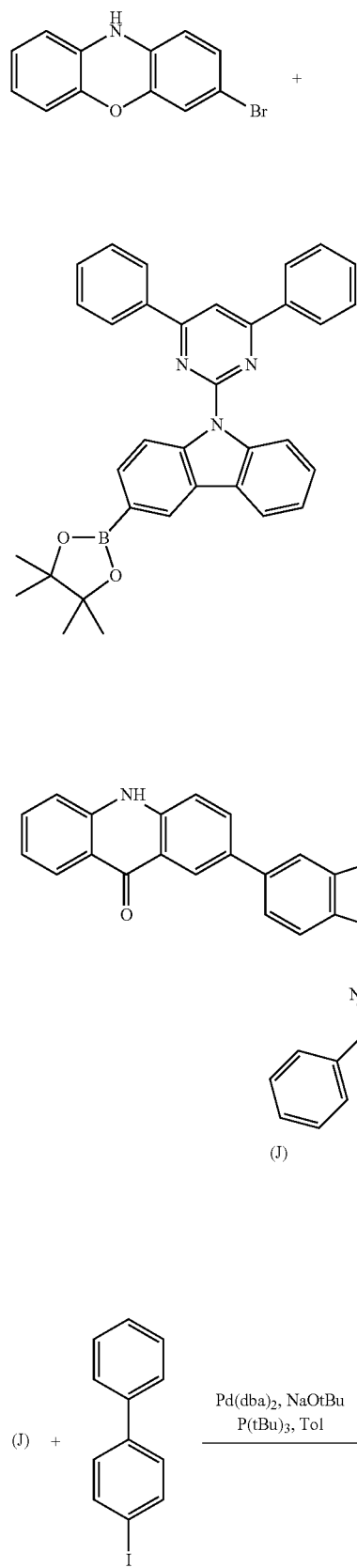

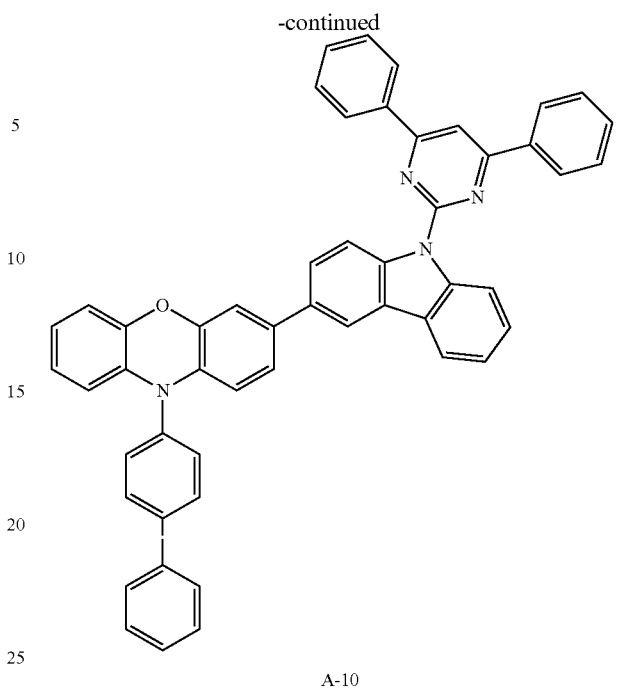

A-10

First Step: Synthesis of Intermediate Product (J)

5.00 g (19.08 mmol) of 3-bromo-10H-phenoxazine, 11.98 g (22.89 mmol) of 9-(4,6-diphenylpyrimidin-2-yl)-3-(4,4,5,5-tetramethyl-1,3,2-dioxaborolan-2-yl)-9H-carbazole, 2.20 g (1.91 mmol) of tetrakis triphenylphosphine palladium (0) (Pd(PPh$_3$)$_4$), and 7.91 g (57.23 mmol) of potassium carbonate are put in a mixed solution prepared by mixing 30 mL of toluene, 30 mL of tetrahydrofuran, and 30 mL of water, and the mixture is refluxed and agitated. When the reaction is complete, the agitated mixture is cooled down to room temperature and precipitated in 1 L of methanol. Then, a precipitate produced therein is extracted therefrom, and heated and dissolved in 1 L of chlorobenzene and pressure-reducing filtered through acid clay/silica gel. The filtered solution is concentrated down to 100 ml and precipitated in 1 L of methanol, obtaining 5.24 g of an intermediate compound (J) (yield: 49%).

Second Step: Synthesis of Chemical Formula A-10

5.72 g (10.11 mmol) of the intermediate compound (J), 5.67 g (20.22 mmol) of 4-iodo-1,1'-biphenyl, 0.58 g (1.01 mmol) of Pd(dba)$_2$, 0.82 g (2.02 mmol) of tri-tert-butyl-phosphine ("TTBP"), and 1.94 g (20.22 mmol) of sodium tert-butoxide are put in 55 mL of toluene, and the mixture is heated and agitated. When the reaction is complete, the agitated mixture is cooled down to room temperature and precipitated in methanol. The precipitate is heated and dissolved in 1 L of chlorobenzene and pressure-reducing filtered through silica gel. The filtered solution is concentrated down to 100 ml and precipitated in 1 L of methanol, obtaining 4.56 g of a compound represented by Chemical Formula A-10 (yield: 62%).

Example 11

Synthesis of Compound A-11

The compound A-11, as an example of a compound for an organic optoelectronic device is synthesized according to the following Reaction Scheme 11.

Reaction Scheme 11

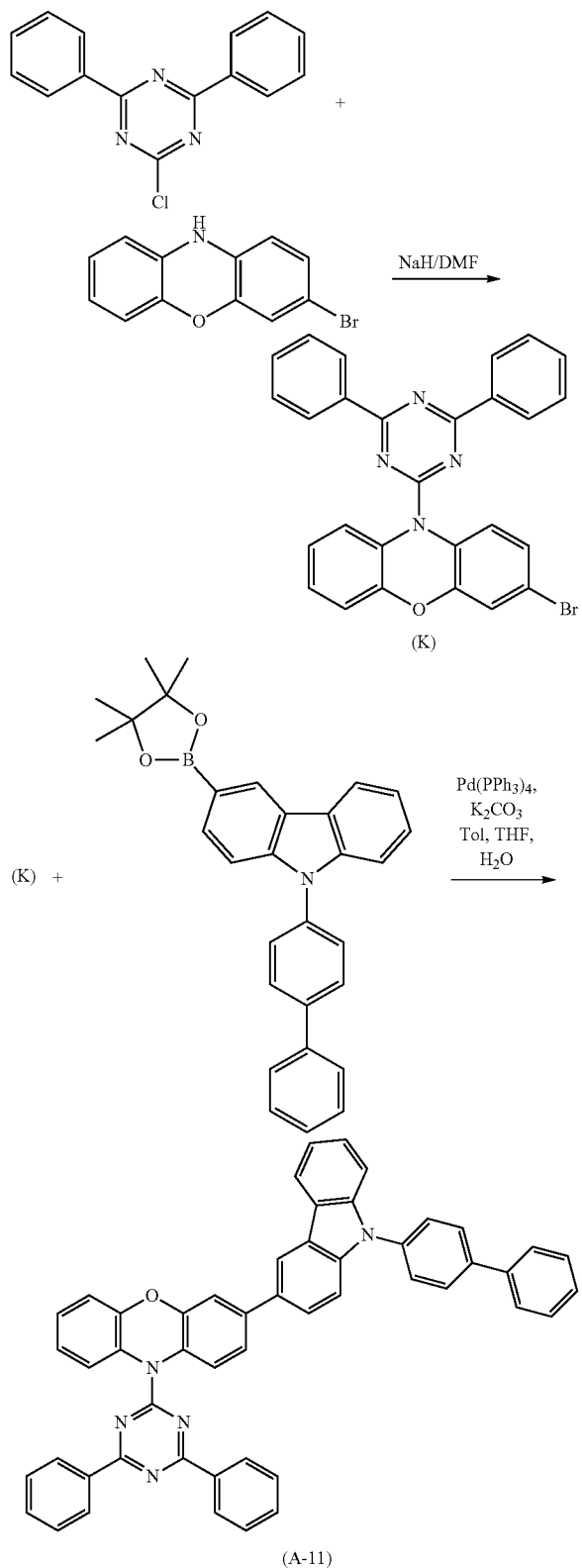

First Step: Synthesis of Intermediate Product (K)

5.00 g (19.09 mmol) of 3-bromo-10H-phenoxazine is dissolved in 80 ml of DMF. The solution is cooled down to 0° C. Next, 0.92 g (22.91 mmol) of sodium hydride (NaH) is slowly added to the reaction solution, and the mixture is agitated at room temperature (20-30° C.) for one hour. Then, 6.13 g (22.91 mmol) of 2-chloro-4,6-diphenyl-1,3,5-triazine is added to the reactant, and the mixture is agitated at room temperature. When the reaction is complete, 200 ml of water is added to the agitated mixture. The mixture is agitated at room temperature for 10 minutes, and 40 ml of methylene chloride is used to perform an extraction three times. Next, 10 g of magnesium sulfate is added to the extract, and the mixture is agitated form 5 minutes and then filtered under a reduced pressure and concentrated under a reduced pressure. The concentrated product is recrystallized using ethyl acetate/n-hexane, obtaining 5.92 g of an intermediate compound (K) (yield: 63%).

Second Step: Synthesis of Chemical Formula A-11

5.90 g (11.96 mmol) of the intermediate compound (K), 6.39 g (14.35 mmol) of 9-([1,1'-biphenyl]-4-yl)-3-(4,4,5,5-tetramethyl-1,3,2-dioxaborolan-2-yl)-9H-carbazole, 1.38 g (1.20 mmol) of tetrakis triphenylphosphine palladium (0) (Pd(PPh$_3$)$_4$), and 4.96 g (35.87 mmol) of potassium carbonate are put in a mixed solution prepared by mixing 20 mL of toluene, 20 mL of tetrahydrofuran, and 20 mL of water, and the mixture is refluxed and agitated. When the reaction is complete, the agitated mixture is poured into 1 L of methanol to obtain a precipitate, and the precipitate is heated and dissolved in 1 L of chlorobenzene. The solution is filtered through silica gel under a reduced pressure, obtaining 4.38 g of a compound A-11 (yield: 50%).

Example 12

Synthesis of Compound A-12

The compound A-12 as an example of a compound for an organic optoelectronic device is synthesized according to the following Reaction Scheme 12.

Reaction Scheme 12

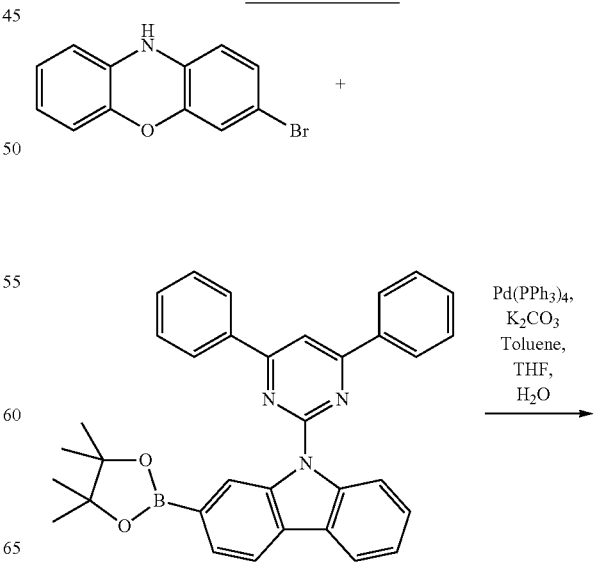

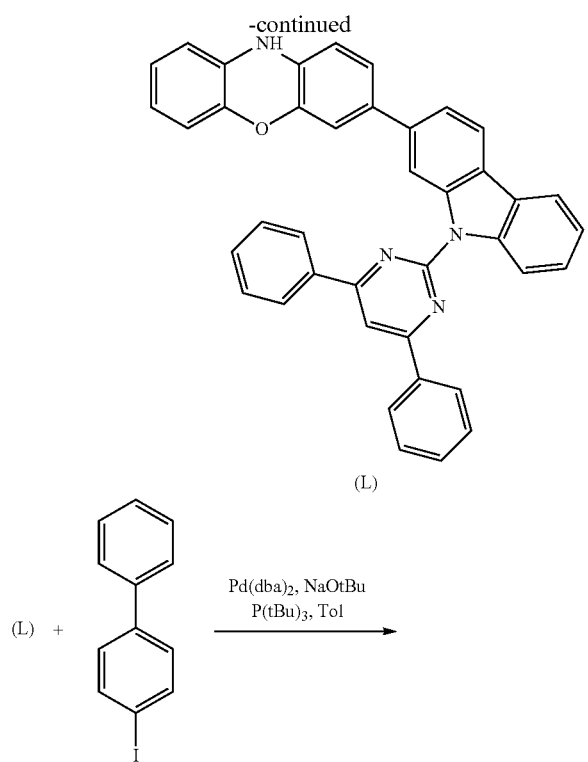

(L)

A-12 temperature and precipitated in 1 L of methanol. Then, a precipitate produced therein is extracted, and then heated and dissolved in 1 L of chlorobenzene and pressure-reducing filtered through acid clay/silica gel. The filtered solution is concentrated down to 100 ml and precipitated in 1 L of methanol, obtaining 5.71 g of an intermediate compound (L) (yield: 53%).

Second Step: Synthesis of Chemical Formula A-12

5.71 g (10.10 mmol) of the intermediate compound (L), 5.67 g (20.19 mmol) of 4-iodo-1,1'-biphenyl, 0.58 g (1.01 mmol) of Pd(dba)$_2$, 0.82 g (2.02 mmol) of tri-tert-butyl-phosphine ("TTBP"), and 1.94 g (20.19 mmol) of sodium tert-butoxide are put in 55 mL of toluene. The mixture is heated and agitated. When the reaction is complete, the agitated mixture is cooled down to room temperature and precipitated in methanol. Then, a precipitate produced therein is heated and dissolved in 1 L of 1,2-dichlorobenzene and pressure-reducing filtered through silica gel. The filtered solution is concentrated down to 100 ml and precipitated in 1 L of methanol, obtaining 4.16 g of a compound represented by Chemical Formula A-12 (yield: 56%).

Example 13

Synthesis of Compound A-13

The compound A-13, as an example of a compound for an organic optoelectronic device according to the present disclosure is synthesized according to the following Reaction Scheme 13.

Reaction Scheme 13

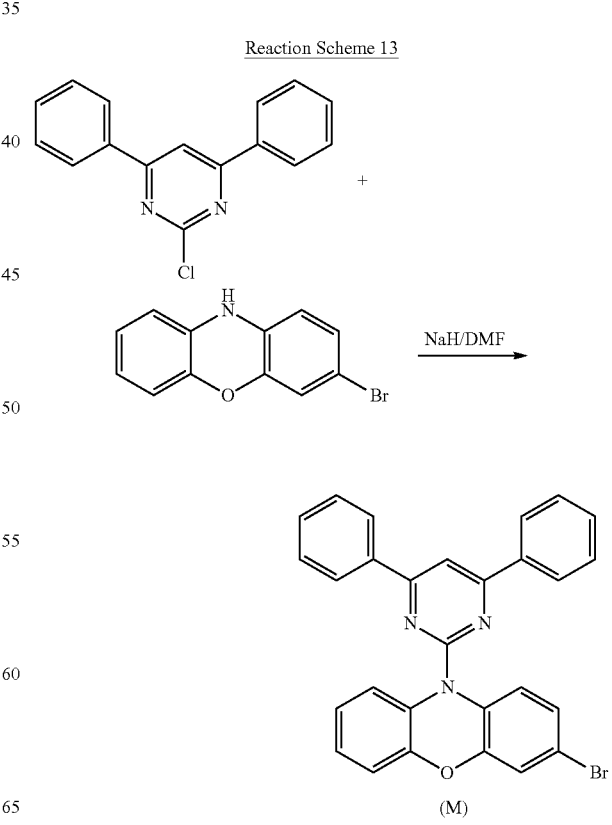

(M)

First Step: Synthesis of Intermediate Product (L)

5.00 g (19.08 mmol) of 3-bromo-10H-phenoxazine, 11.98 g (22.89 mmol) of 9-(4,6-diphenylpyrimidin-2-yl)-2-(4,4,5,5-tetramethyl-1,3,2-dioxaborolan-2-yl)-9H-carbazole, 2.20 g (1.91 mmol) of tetrakis triphenylphosphine palladium (0) (Pd(PPh$_3$)$_4$), and 7.91 g (57.23 mmol) of potassium carbonate are put in a mixed solution prepared by mixing 35 mL of toluene, 35 mL of tetrahydrofuran, and 35 mL of water, and the mixture is refluxed and agitated. When the reaction is complete, the agitated mixture is cooled down to room

53

-continued (M) +

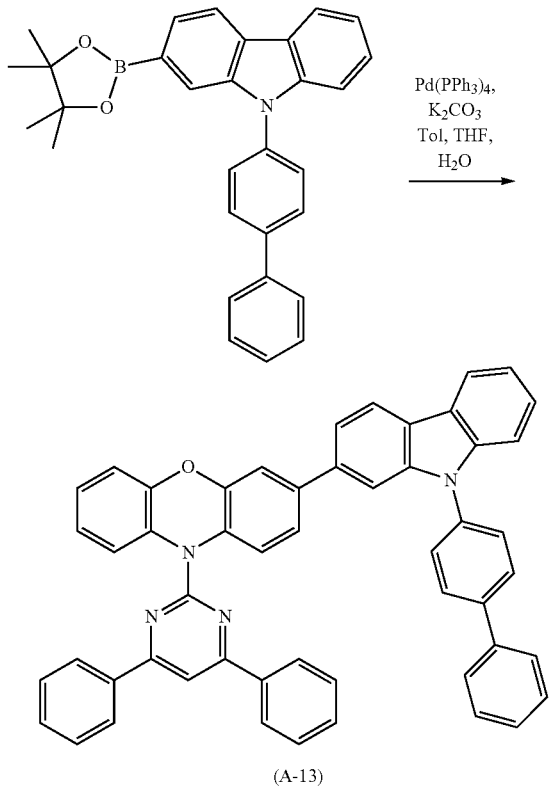

(A-13)

First Step: Synthesis of Intermediate Product (M)

5.00 g (19.09 mmol) of 3-bromo-10H-phenoxazine is dissolved in 80 ml of DMF, and the reaction solution is cooled down to 0° C. Next, 0.92 g (22.91 mmol) of sodium hydride (NaH) is slowly added to the reaction solution. The mixture is agitated at room temperature (20-30° C.) for one hour. Then, 6.11 g (22.91 mmol) of 2-chloro-2-chloro-4,6-diphenylpyrimidine is added to the reactant, and the mixture is agitated at room temperature. When the reaction is complete, 200 ml of water is added to the agitated mixture. The obtained mixture is agitated at room temperature for 10 minutes, and 40 ml of methylene chloride is used to perform an extraction three times. Then, 10 g of magnesium sulfate is added to the extract, and the mixture is agitated for 5 minutes, and then filtered under a reduced pressure and concentrated under a reduced pressure. The concentrated product is recrystallized using ethyl acetate/n-hexane, obtaining 5.77 g of an intermediate compound (M) (yield: 61%).

Second Step: Synthesis of Chemical Formula A-13

5.77 g (11.73 mmol) of the intermediate compound (M), 6.27 g (14.07 mmol) of 9-([1,1'-biphenyl]-4-yl)-2-(4,4,5,5-tetramethyl-1,3,2-dioxaborolan-2-yl)-9H-carbazole, 1.35 g (1.17 mmol) of tetrakis triphenylphosphine palladium (0) (Pd(PPh$_3$)$_4$), and 4.86 g (35.18 mmol) of potassium carbonate are put in a mixed solution prepared by mixing 20 mL of toluene, 20 mL of tetrahydrofuran, and 20 mL of water, and the mixture is refluxed and agitated. When the reaction is complete, the agitated mixture is poured into 1 L of methanol to obtain a precipitate. The precipitate is heated and dissolved in 1 L of 1,2-dichlorobenzene and filtered through silica gel under a reduced pressure, obtaining 4.19 g of a compound A-13 (yield: 49%).

54

Manufacture of Organic Light Emitting Diode

Example 14

Manufacture of Organic Light Emitting Diode

First Step: Preparation of Composition for Organic Light Emitting Diode

The host compound synthesized according to Example 1 is doped with 10 percent by weight ("weight %") of Ir(ppy)$_3$, preparing a mixture for an emission layer. Then, 1 weight % of the mixture for an emission layer is dissolved in a toluene solvent, preparing a composition for an organic photoelectric device.

Second Step: Manufacture of Organic Light Emitting Diode

First, a transparent electrode substrate is fabricated by coating ITO (indium-tin oxide) on a glass substrate, cleaning it, patterning the ITO using a photosensitive resin and an etchant, and cleaning it again. Then, PEDOT (Batron P 4083, Bayer Inc.) is coated to be about 55 nm thick on the ITO and fired at 180° C. for about one hour, forming a hole injection layer ("HIL"). Then, the composition for an organic optoelectronic device prepared in the first step is spin-coated on the hole injection layer ("HIL") and fired in a vacuum oven to completely remove a solvent and form an emission layer. Herein, the composition for an emission layer is filtered through a 0.2 millimeters ("mm") filter before the spin-coating. The emission layer is formed to be about 45 nm thick by controlling the concentration and spin-coating speed of the composition. Then, an electron transport layer ("ETL") is formed by respectively vacuum-depositing ET202 and LiQ to be 15 nm thick on the emission layer with a vacuum depositor, while a vacuum degree of less than or equal to 4×10$^{-6}$ Torr is maintained. Al is sequentially deposited to be 120 nm thick to form a cathode on the electron transport layer ("ETL"). During the deposition, the thickness and speed of the cathode are controlled using a crystal sensor.

The organic light emitting diode is specifically manufactured to have a structure of ITO/PEDOT:PSS (55 nm)/EML (host compound (90 weight %)+dopant compound (10 weight %), 45 nm)/ET202 (15 nm)/LiQ (15 nm)/Al (120 nm).

Example 15

Manufacture of Organic Light Emitting Diode

An organic light emitting diode is manufactured according to the same method as Example 14, except for using the host compound synthesized according to Example 2 instead of the one according to Example 1.

Example 16

Manufacture of Organic Light Emitting Diode

An organic light emitting diode is manufactured according to the same method as Example 14, except for using the host compound synthesized according to Example 3 instead of the one according to Example 1.

Example 17

Manufacture of Organic Light Emitting Diode

An organic light emitting diode is manufactured according to the same method as Example 14, except for using the host compound synthesized according to Example 4 instead of the one according to Example 1.

Example 18

Manufacture of Organic Light Emitting Diode

An organic light emitting diode is manufactured according to the same method as Example 14, except for using the host compound synthesized according to Example 5 instead of the one according to Example 1.

Example 19

Manufacture of Organic Light Emitting Diode

An organic light emitting diode is manufactured according to the same method as Example 14, except for using the host compound synthesized according to Example 6 instead of the one according to Example 1.

Example 20

Manufacture of Organic Light Emitting Diode

An organic light emitting diode is manufactured according to the same method as Example 14, except for using the host compound synthesized according to Example 7 instead of the one according to Example 1.

Example 21

Manufacture of Organic Light Emitting Diode

An organic light emitting diode is manufactured according to the same method as Example 14, except for using the host compound synthesized according to Example 8 instead of the one according to Example 1.

Example 22

Manufacture of Organic Light Emitting Diode

An organic light emitting diode is manufactured according to the same method as Example 14, except for using the host compound synthesized according to Example 9 instead of the one according to Example 1.

Example 23

Manufacture of Organic Light Emitting Diode

An organic light emitting diode is manufactured according to the same method as Example 14, except for using the host compound synthesized according to Example 10 instead of the one according to Example 1.

Example 24

Manufacture of Organic Light Emitting Diode

An organic light emitting diode is manufactured according to the same method as Example 14, except for using the host compound synthesized according to Example 11 instead of the one according to Example 1.

Example 25

Manufacture of Organic Light Emitting Diode

An organic light emitting diode is manufactured according to the same method as Example 14, except for using the host compound synthesized according to Example 12 instead of the one according to Example 1.

Example 26

Manufacture of Organic Light Emitting Diode

An organic light emitting diode is manufactured according to the same method as Example 14, except for using the host compound synthesized according to Example 13 instead of the one according to Example 1.

Comparative Example 1

Manufacture of Organic Light Emitting Diode

An organic light emitting diode is fabricated according to the same method as Example 14, except for using a mixture of PVK (polyvinylcarbazole) and PBD (2-(4-biphenyl)-5-(4-t-butylphenyl)-1,3,4-oxadiazole) represented by the following Chemical Formulae in a weight ratio of 1:1 as a host instead of the host compound synthesized according to Example 1.

The Ir(ppy)$_3$, PVK, and PBD used to fabricate the organic light emitting diode have the following structures.

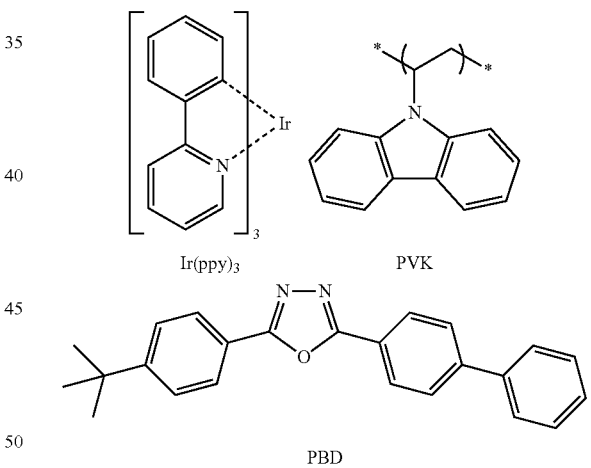

Ir(ppy)$_3$        PVK

PBD

Performance Measurement of Organic Light Emitting Diode

Each organic light emitting diode according to Examples 14 to 26 and Comparative Example 1 is measured regarding current density change depending upon the voltage, luminance change, and luminous efficiency. The specific methods are as follows. The results are shown in the following Table 1.

(1) Measurement of Current Density Change Depending on Voltage Change

The obtained organic light emitting diodes are measured regarding current value flowing in a unit device, while their voltages are increased from 0 Volts ("V") to 10 V using a current-voltage meter (Keithley 2400). The measured current value is divided by area to calculate current density.

(2) Measurement of Luminance Change Depending on Voltage Change

The organic light emitting diodes are measured regarding luminance using a luminance meter (Minolta Cs-1000A) while their voltages are increased from 0 V to 10 V.

(3) Measurement of Luminous Efficiency

Current efficiency (candelas per ampere, cd/A) and electric power efficiency (lumens per watt, lm/W) at the same luminance (1000 cd/m$^2$) are calculated by using luminance and current density from (1) and (2) and a voltage.

TABLE 1

|  | Results at 1000 cd/m$^2$ | | | |
| --- | --- | --- | --- | --- |
|  | Driving voltage (V) | Current efficiency (cd/A) | Electric power efficiency (lm/W) | Color coordinates (x, y) |
| Example 14 | 5.0 | 19.6 | 14.2 | 0.363, 0.610 |
| Example 15 | 5.2 | 17.8 | 11.9 | 0.361, 0.607 |
| Example 16 | 4.9 | 24.9 | 12.2 | 0.367, 0.613 |
| Example 17 | 5.3 | 16.4 | 11.7 | 0.361, 0.609 |
| Example 18 | 5.5 | 17.6 | 10.9 | 0.362, 0.603 |
| Example 19 | 5.3 | 19.5 | 16.1 | 0.362, 0.613 |
| Example 20 | 4.8 | 25.0 | 17.4 | 0.365, 0.609 |
| Example 21 | 5.2 | 22.1 | 17.5 | 0.371, 0.601 |
| Example 22 | 5.4 | 15.1 | 8.9 | 0.363, 0.612 |
| Example 23 | 5.5 | 16.3 | 9.5 | 0.368, 0.614 |
| Example 24 | 5.3 | 17.2 | 14.1 | 0.361, 0.612 |
| Example 25 | 5.6 | 14.8 | 9.1 | 0.363, 0.607 |
| Example 26 | 5.3 | 18.7 | 13.7 | 0.370, 0.601 |
| Comparative Example 1 | 5.1 | 13.2 | 8.1 | 0.365, 0.610 |

Referring to the results in Table 1, the host materials used in Examples 1 to 8 show excellent device performance in terms of luminous efficiency, electric power efficiency, and the like compared with that used in Comparative Example 1. Specifically, the host materials used in Example 16 and 20 show excellent device performance in terms of driving voltage, current efficiency, electric power efficiency, and the like compared with the one according to Comparative Example 1. Accordingly, the host materials may realize an organic light emitting diode having a low voltage, high efficiency, high luminance, and a long life-span.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present disclosure in any way.

What is claimed is:

1. A compound for an organic optoelectronic device represented by Chemical Formula 1:

Chemical Formula 1

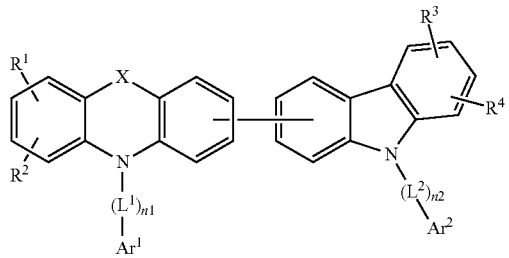

wherein, in Chemical Formula 1,

X is —S—, —C(=O)—, or —O—, $R^1$ to $R^4$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted monocyclic or bicyclic C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, $L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, $Ar^1$ and $Ar^2$ are each independently a substituted or unsubstituted C6 to C30 aryl group or a substituted or unsubstituted C2 to C30 heteroaryl group, wherein "substituted" in the definitions of $Ar^1$ and $Ar^2$ refers to one substituted within deuterium, a halogen, a hydroxy group, an amino group, a C1 to C30 amine group, a nitro group, a C1 to C30 alkyl group, a C3 to C30 cycloalkyl group, a C6 to C30 aryl group, a C1 to C20 alkoxy group, a fluoro group, a C1 to C10 trifluoroalkyl group or a cyano group instead of at least one hydrogen of a substituting group, and at least one of $Ar^1$ and $Ar^2$ is a substituted or unsubstituted C2 to C30 heteroaryl group.

2. The compound for an organic optoelectronic device of claim 1, wherein the compound for an organic optoelectronic device is represented by Chemical Formula 2:

Chemical Formula 2

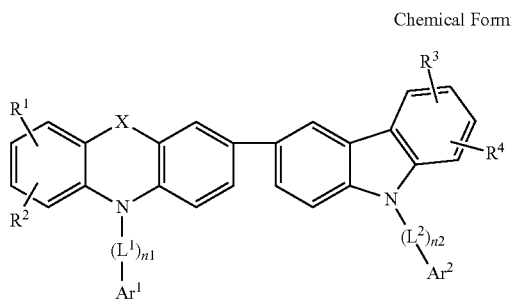

wherein, in Chemical Formula 2,
X is —S—, —C(=O)—, or —O—,
$R^1$ to $R^4$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted monocyclic or bicyclic C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof,
$L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof,
n1 and n2 are each independently integers ranging from 0 to 3,
$Ar^1$ and $Ar^2$ are each independently a substituted or unsubstituted C6 to C30 aryl group or a substituted or unsubstituted C2 to C30 heteroaryl group, wherein "substituted" in the definitions of $Ar^1$ and $Ar^2$ refers to one substituted within deuterium, a halogen, a hydroxy group, an amino group, a C1 to C30 amine group, a nitro group, a C1 to C30 alkyl group, a C3 to C30 cycloalkyl group, a C6 to C30 aryl group, a C1 to C20 alkoxy group, a fluoro group, a C1 to C10 trifluoroalkyl group or a cyano group instead of at least one hydrogen of a substituting group, and
at least one of $Ar^1$ and $Ar^2$ is a substituted or unsubstituted C2 to C30 heteroaryl group.

3. The compound for an organic optoelectronic device of claim 1, wherein the compound for an organic optoelectronic device is represented by Chemical Formula 3:

Chemical Formula 3

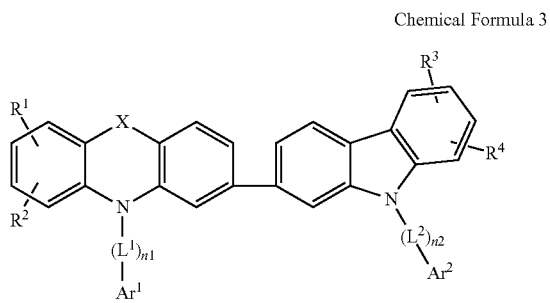

wherein, in Chemical Formula 3,
X is —S—, —C(=O)—, or —O—,
$R^1$ to $R^4$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted monocyclic or bicyclic C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof,
$L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof,
n1 and n2 are each independently integers ranging from 0 to 3,
$Ar^1$ and $Ar^2$ are each independently a substituted or unsubstituted C6 to C30 aryl group or a substituted or unsubstituted C2 to C30 heteroaryl group, wherein "substituted" in the definitions of $Ar^1$ and $Ar^2$ refers to one substituted within deuterium, a halogen, a hydroxy group, an amino group, a C1 to C30 amine group, a nitro group, a C1 to C30 alkyl group, a C3 to C30 cycloalkyl group, a C6 to C30 aryl group, a C1 to C20 alkoxy group, a fluoro group, a C1 to C10 trifluoroalkyl group or a cyano group instead of at least one hydrogen of a substituting group, and
at least one of $Ar^1$ and $Ar^2$ is a substituted or unsubstituted C2 to C30 heteroaryl group.

4. The compound for an organic optoelectronic device of claim 1, wherein the compound for an organic optoelectronic device is represented by Chemical Formula 4:

Chemical Formula 4

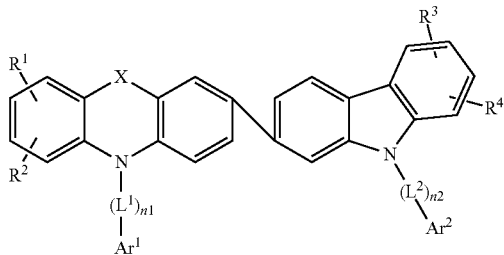

wherein, in Chemical Formula 4,

X is —S—, —C(=O)—, or —O—, $R^1$ to $R^4$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted monocyclic or bicyclic C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, $L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, $Ar^1$ and $Ar^2$ are each independently a substituted or unsubstituted C6 to C30 aryl group or a substituted or unsubstituted C2 to C30 heteroaryl group, wherein "substituted" in the definitions of $Ar^1$ and $Ar^2$ refers to one substituted within deuterium, a halogen, a hydroxy group, an amino group, a C1 to C30 amine group, a nitro group, a C1 to C30 alkyl group, a C3 to C30 cycloalkyl group, a C6 to C30 aryl group, a C1 to C20 alkoxy group, a fluoro group, a C1 to C10 trifluoroalkyl group or a cyano group instead of at least one hydrogen of a substituting group, and at least one of $Ar^1$ and $Ar^2$ is a substituted or unsubstituted C2 to C30 heteroaryl group.

5. The compound for an organic optoelectronic device of claim 1, wherein the compound for an organic optoelectronic device is represented by Chemical Formula 5:

Chemical Formula 5

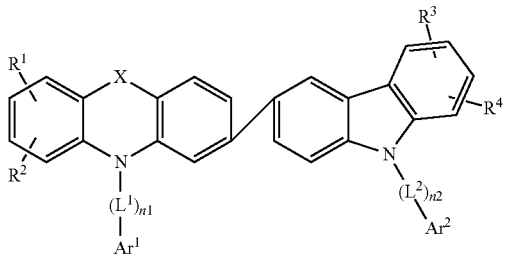

wherein, in Chemical Formula 5,

X is —S—, —C(=O)—, or —O—, $R^1$ to $R^4$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted monocyclic or bicyclic C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, $L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 and n2 are each independently integers ranging from 0 to 3, $Ar^1$ and $Ar^2$ are each independently a substituted or unsubstituted C6 to C30 aryl group or a substituted or unsubstituted C2 to C30 heteroaryl group, wherein "substituted" in the definitions of $Ar^1$ and $Ar^2$ refers to one substituted within deuterium, a halogen, a hydroxy group, an amino group, a C1 to C30 amine group, a nitro group, a C1 to C30 alkyl group, a C3 to C30 cycloalkyl group, a C6 to C30 aryl group, a C1 to C20 alkoxy group, a fluoro group, a C1 to C10 trifluoroalkyl group or a cyano group instead of at least one hydrogen of a substituting group, and at least one of $Ar^1$ and $Ar^2$ is a substituted or unsubstituted C2 to C30 heteroaryl group.

6. The compound for an organic optoelectronic device of claim 1, wherein X is —C(=O)— or —O—.

7. The compound for an organic optoelectronic device of claim 1, wherein $Ar^1$ is a substituted or unsubstituted C2 to C30 heteroaryl group, and $Ar^2$ is a substituted or unsubstituted C6 to C30 aryl group.

8. The compound for an organic optoelectronic device of claim 1, wherein $Ar^2$ is a substituted or unsubstituted C2 to C30 heteroaryl group, and $Ar^1$ is a substituted or unsubstituted C6 to C30 aryl group.

9. The compound for an organic optoelectronic device of claim 1, wherein the at least one of $Ar^1$ and $Ar^2$ is a substituted or unsubstituted quinolinylene group, a substituted or unsubstituted isoquinolinylene group, a substituted or unsubstituted pyridinylene group, a substituted or unsubstituted pyrimidinylene group, a substituted or unsubstituted triazinylene group, a substituted or unsubstituted furanyl group, a substituted or unsubstituted benzofuranyl group, a substituted or unsubstituted isofuranyl group, a substituted or unsubstituted benzoisofuranyl group, a substituted or unsubstituted oxazoline group, a substituted or unsubstituted benzoxazoline group, a substituted or unsubstituted oxadiazolyline group, a substituted or unsubstituted benzooxadiazolyline group, a substituted or unsubstituted thiophenyl group, a substituted or unsubstituted benzothiophenyl group, a substituted or unsubstituted isothiozoline group, a substituted or unsubstituted benzoisothiozoline group, a substituted or unsubstituted thiozoline group, a substituted or unsubstituted benzothiozoline group, a substituted or unsubstituted pyridazinyl group, a substituted or unsubstituted benzopyridazinyl group, a substituted or unsubstituted pyrazinyl group substituted or unsubstituted benzopyrazinyl group, or a combination thereof, wherein "substituted" in the definitions of $Ar^1$ and $Ar^2$ refers to one substituted within deuterium, a halogen, a hydroxy group, an amino group, a C1 to C30 amine group, a nitro group, a C1 to C30 alkyl group, a C3 to C30 cycloalkyl group, a C6 to C30 aryl group, a C1 to C20 alkoxy group, a fluoro group, a C1 to C10 trifluoroalkyl group or a cyano group instead of at least one hydrogen of a substituting group.

10. The compound for an organic optoelectronic device of claim 1, wherein the at least one of $Ar^1$ and $Ar^2$ is one of Chemical Formulae X-1 to X-5:

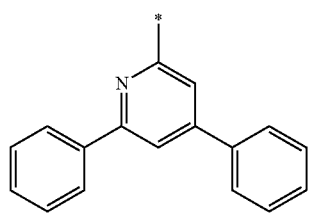

Chemical Formula X-1

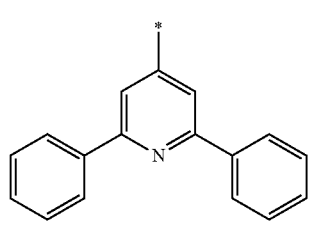

Chemical Formula X-2

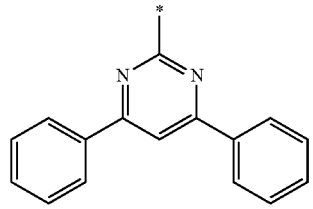

Chemical Formula X-3

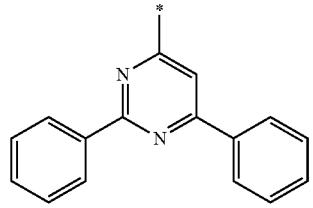

Chemical Formula X-4

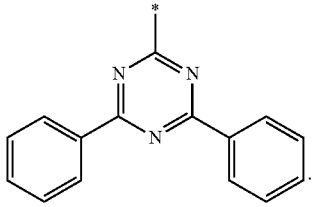

Chemical Formula X-5

11. The compound for an organic optoelectronic device of claim 1, wherein the compound for an organic optoelectronic device is one of Chemical Formulae A-1 to A-13

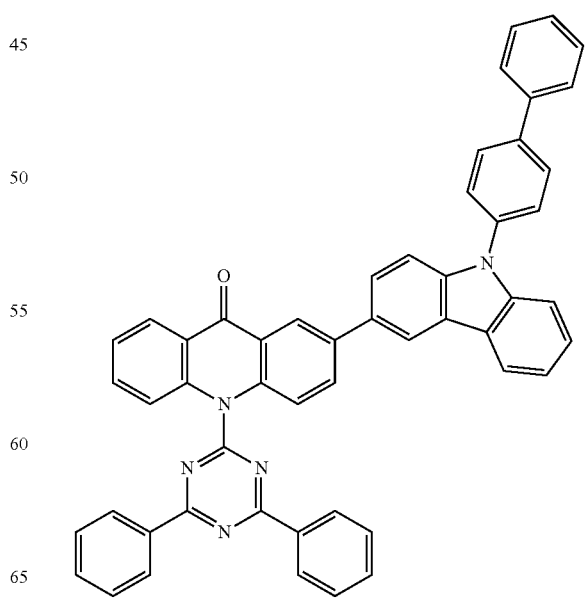

A-1

-continued
A-2
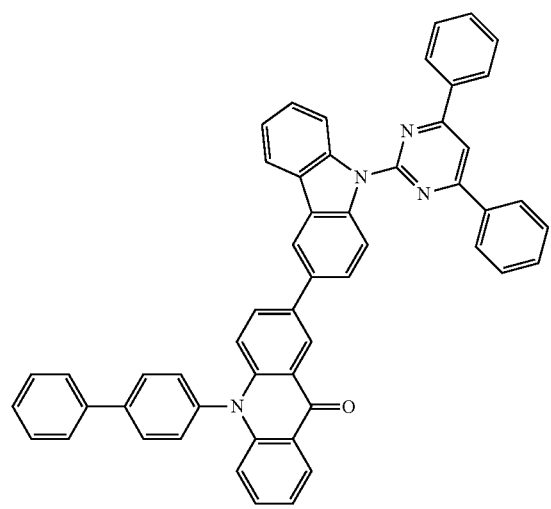
A-3
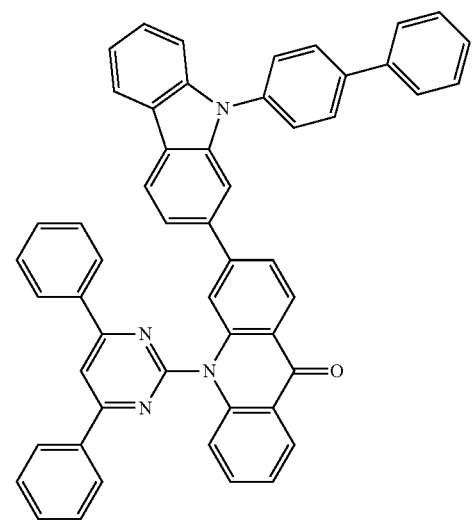
A-4
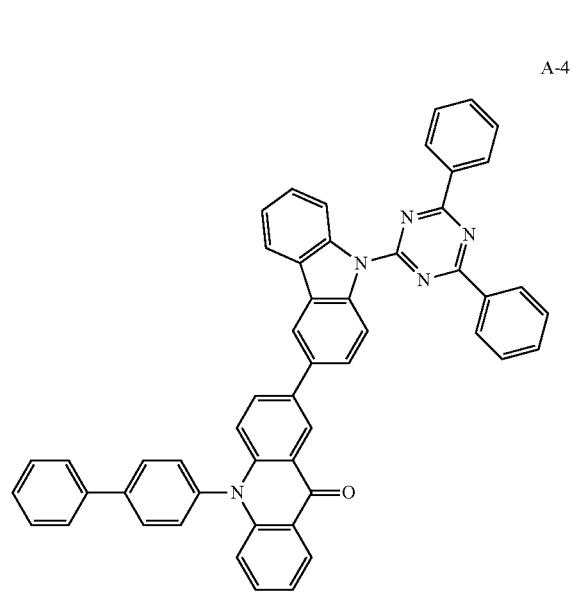
-continued
A-5
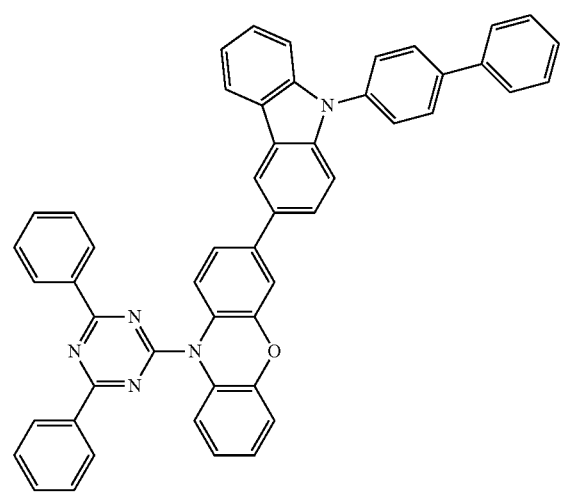
A-6
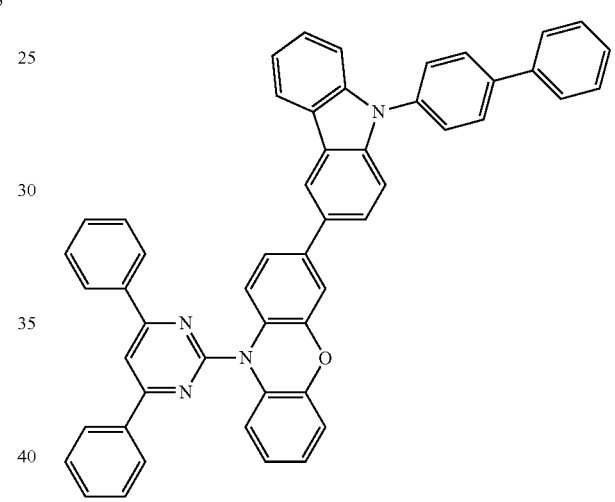
A-7
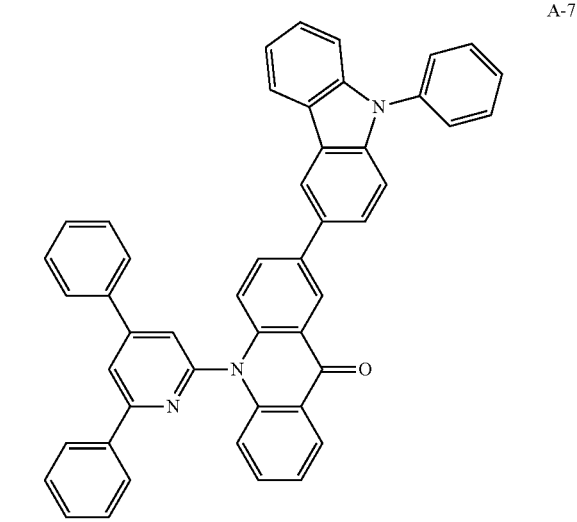

A-8
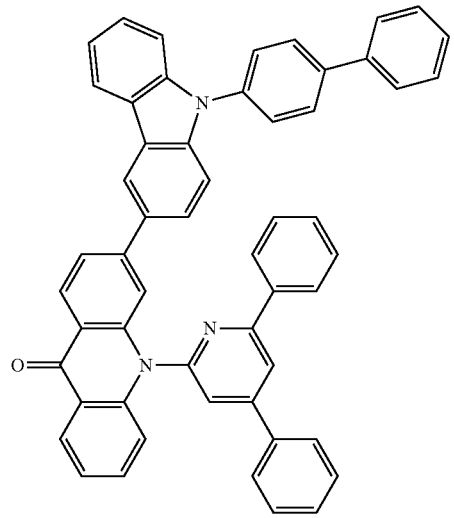
A-9
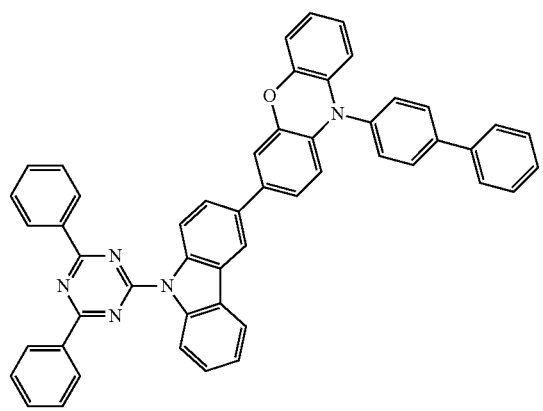
A-10
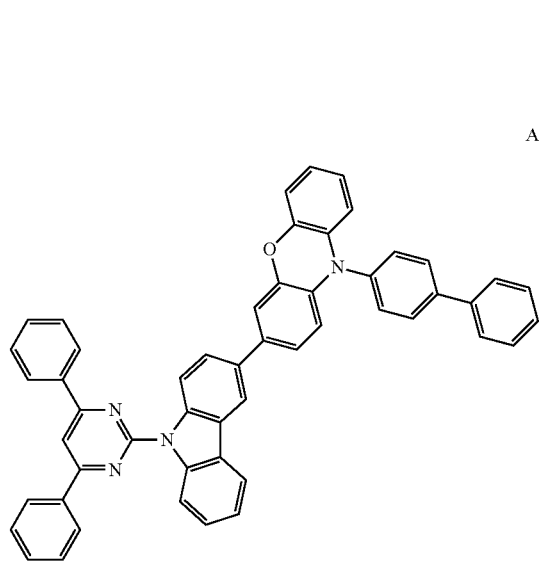
A-11
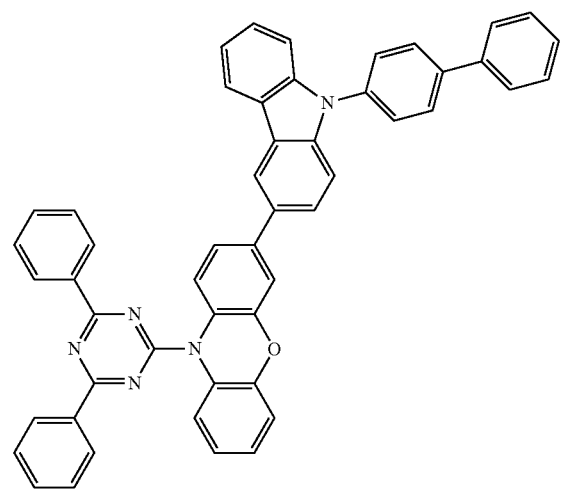
A-12
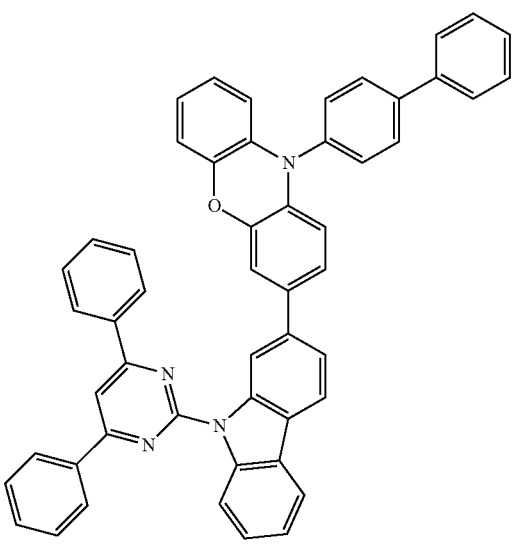
A-13
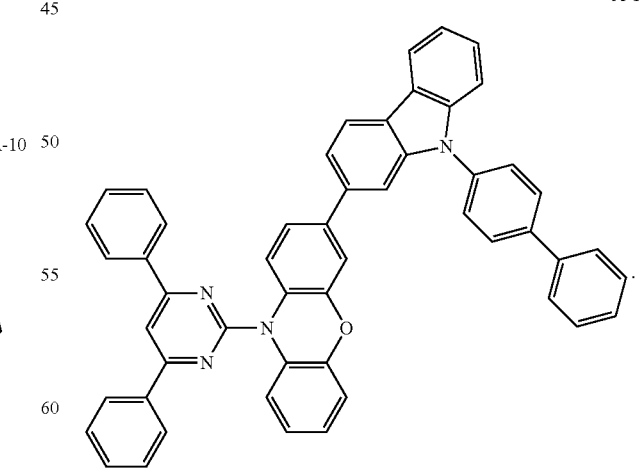
12. The compound for an organic optoelectronic device of claim 1, wherein the organic optoelectronic device is selected from an organic photoelectric device, an organic light emitting diode, an organic solar cell, an organic transistor, an organic photoconductor drum, and an organic memory device.

13. An organic light emitting diode, comprising
an anode, a cathode, and at least one organic thin layer between the anode and the cathode,
wherein the at least one organic thin layer comprises the compound for an organic optoelectronic device according to claim 1.

14. The organic light emitting diode of claim 13, wherein the organic thin layer is selected from an emission layer, a hole transport layer, a hole injection layer, an electron transport layer, an electron injection layer, a hole blocking layer, and a combination thereof.

15. The organic light emitting diode of claim 14, wherein the emission layer comprises the compound for an organic optoelectronic device.

16. The organic light emitting diode of claim 14, wherein the emission layer comprises a phosphorescent or fluorescent host material comprising the compound for an organic optoelectronic device.

17. A display device comprising the organic light emitting diode according to claim 13.

18. The display device of claim 17, wherein X is —C(=O)— or —O—.

19. The display device of claim 17, wherein $Ar^1$ is a substituted or unsubstituted C2 to C30 heteroaryl group, and $Ar^2$ is a substituted or unsubstituted C6 to C30 aryl group.

20. The display device of claim 17, wherein $Ar^2$ is a substituted or unsubstituted C2 to C30 heteroaryl group, and $Ar^1$ is a substituted or unsubstituted C6 to C30 aryl group.

21. A compound for an organic optoelectronic device represented by Chemical Formula 1:

Chemical Formula 1

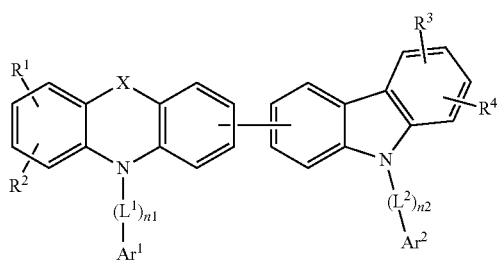

wherein, in Chemical Formula 1,
X is —NR'—, —S—, —SO$_2$—, —C(=O)—, or —O—,
$R^1$ to $R^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted monocyclic or bicyclic C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof,
$L^1$ and $L^2$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof,
n1 and n2 are each independently integers ranging from 0 to 3,
$Ar^1$ and $Ar^2$ are each independently a substituted or unsubstituted C6 to C30 aryl group or a substituted or unsubstituted C2 to C30 heteroaryl group, and
at least one of $Ar^1$ and $Ar^2$ is a substituted or unsubstituted quinolinyl group, a substituted or unsubstituted isoquinolinyl group, a substituted or unsubstituted pyridinyl group, a substituted or unsubstituted pyrimidinyl group, a substituted or unsubstituted triazinyl group, a substituted or unsubstituted pyridazinyl group, a substituted or unsubstituted benzopyridazinyl group, a substituted or unsubstituted pyrazinyl group substituted or unsubstituted benzopyrazinyl group, or a combination thereof, wherein "substituted" in the definitions of $Ar^1$ and $Ar^2$ refers to one substituted within deuterium, a halogen, a hydroxy group, an amino group, a C1 to C30 amine group, a nitro group, a C1 to C30 alkyl group, a C3 to C30 cycloalkyl group, a C6 to C30 aryl group, a C1 to C20 alkoxy group, a fluoro group, a C1 to C10 trifluoroalkyl group or a cyano group instead of at least one hydrogen of a substituting group.

22. An organic light emitting diode, comprising
an anode, a cathode, and at least one organic thin layer between the anode and the cathode,
wherein the at least one organic thin layer comprises the compound for an organic optoelectronic device according to claim 21.

23. A display device comprising the organic light emitting diode according to claim 22.

* * * * *